US011370743B2

(12) United States Patent
Wender et al.

(10) Patent No.: US 11,370,743 B2
(45) Date of Patent: Jun. 28, 2022

(54) PRODRUG DERIVATIVES OF PROTEIN KINASE C MODULATORS

(71) Applicant: The Board of Trustees of the Leland Stanford Junior University, Stanford, CA (US)

(72) Inventors: Paul A. Wender, Stanford, CA (US); Katherine N. Keenan, Stanford, CA (US); Nancy Lynn Benner, Stanford, CA (US); Jack Leider Sloane, Stanford, CA (US); Xiaoyu Zang, Stanford, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 166 days.

(21) Appl. No.: 16/604,665

(22) PCT Filed: May 10, 2018

(86) PCT No.: PCT/US2018/032033
§ 371 (c)(1),
(2) Date: Oct. 11, 2019

(87) PCT Pub. No.: WO2018/209062
PCT Pub. Date: Nov. 15, 2018

(65) Prior Publication Data
US 2021/0002203 A1 Jan. 7, 2021

Related U.S. Application Data

(60) Provisional application No. 62/505,247, filed on May 12, 2017.

(51) Int. Cl.
*C07C 69/013* (2006.01)
*A61P 31/18* (2006.01)
*C07C 69/78* (2006.01)
*A61K 9/00* (2006.01)

(52) U.S. Cl.
CPC ............ *C07C 69/013* (2013.01); *A61P 31/18* (2018.01); *C07C 69/78* (2013.01); *A61K 9/007* (2013.01); *A61K 9/0019* (2013.01); *A61K 9/0053* (2013.01); *C07C 2603/40* (2017.05)

(58) Field of Classification Search
None
See application file for complete search history.

(56) References Cited

U.S. PATENT DOCUMENTS

| 8,431,612 | B2 | 4/2013 | Xu et al. |
| 8,816,122 | B2 | 8/2014 | Wender et al. |
| 2011/0014699 | A1 | 1/2011 | Wender et al. |
| 2011/0251421 | A1* | 10/2011 | Xu .......................... A61P 31/18 560/171 |
| 2013/0331446 | A1 | 12/2013 | Grue-Sorensen et al. |
| 2015/0291551 | A1 | 10/2015 | Grue-Sorensen et al. |
| 2016/0107977 | A1 | 4/2016 | Baran et al. |

FOREIGN PATENT DOCUMENTS

JP 08245505 A * 9/1996

OTHER PUBLICATIONS

Pubchem SID 237309815.*
Caplus 1996 759041.*
Teng, R. et al. Fitoterapia 2009 vol. 80 pp. 233-236.*
Pubchem SID 237309815 Deposit Date: Feb. 13, 2015 (Feb. 13, 2015) pp. 1-7.
Blanco-Molina et al. 'Ingenol esters induce apoptosis in Jurkat cells through an AP-1 and NF-UB independent pathway', Chemistry & Biology, 2001, vol. 8, pp. 767-778.
Notification of Transmillal of The international Search Report and the Written Opinion of the International Searching Authority from PCT/US2018/032033.

* cited by examiner

*Primary Examiner* — Heidi Reese
(74) *Attorney, Agent, or Firm* — Thomas | Horstemeyer, LLP

(57) ABSTRACT

Embodiments of prodrugs of PKC modulators that show efficacy coupled with low levels of toxicity and improved stability are provided. The prodrug compounds are useful in academic research (animal studies), as candidates for preclinical research, and as therapeutic agents. By taking advantage of a pharmacophore-based strategy, this design strategy provides access to prodrugs of PKC modulators of diverse scaffolds including tigliane diterpenes, ingenane diterpenes, daphnane diterpene orthoesters, diacylglycerols, and bryostatins, and analogs thereof. In particular, embodiments of the prodrug ingenane esters having substitutions at C20 and their use as therapeutic agents are provided.

5 Claims, 14 Drawing Sheets

| | R | Yield | Hydrolytic stability ($t_{1/2}$) | Esterase stability ($t_{1/2}$) |
|---|---|---|---|---|
| 3 | H | - | >7d | 18 ± 3 h |
| 4a | acetyl | quant. | >7d | 27 ± 3 h |
| 4b | $C_5H_{11}$C(O)- | 48% | >7d | 2.4 ± 0.5 h |
| 4c | $C_9H_{19}$C(O)- | 85% | >7d | 19 ± 2 h |
| 4d | PhC(O)- | 56% | >7d | 32 ± 9 h |
| 4e | ethyl carbonate | 30% | >7d | 4.8 ± 0.6 h |
| 4f | $C_8H_{17}$NHC(O)- | 60% | >7d | 71 ± 13 h |
| 6 | H | - | 18 h | 1.7 ± 0.3 h |
| 7 | $C_9H_{19}$C(O)- | 63% | 2 h (0.5-4 h) | 3.3 ± 0.4 h |

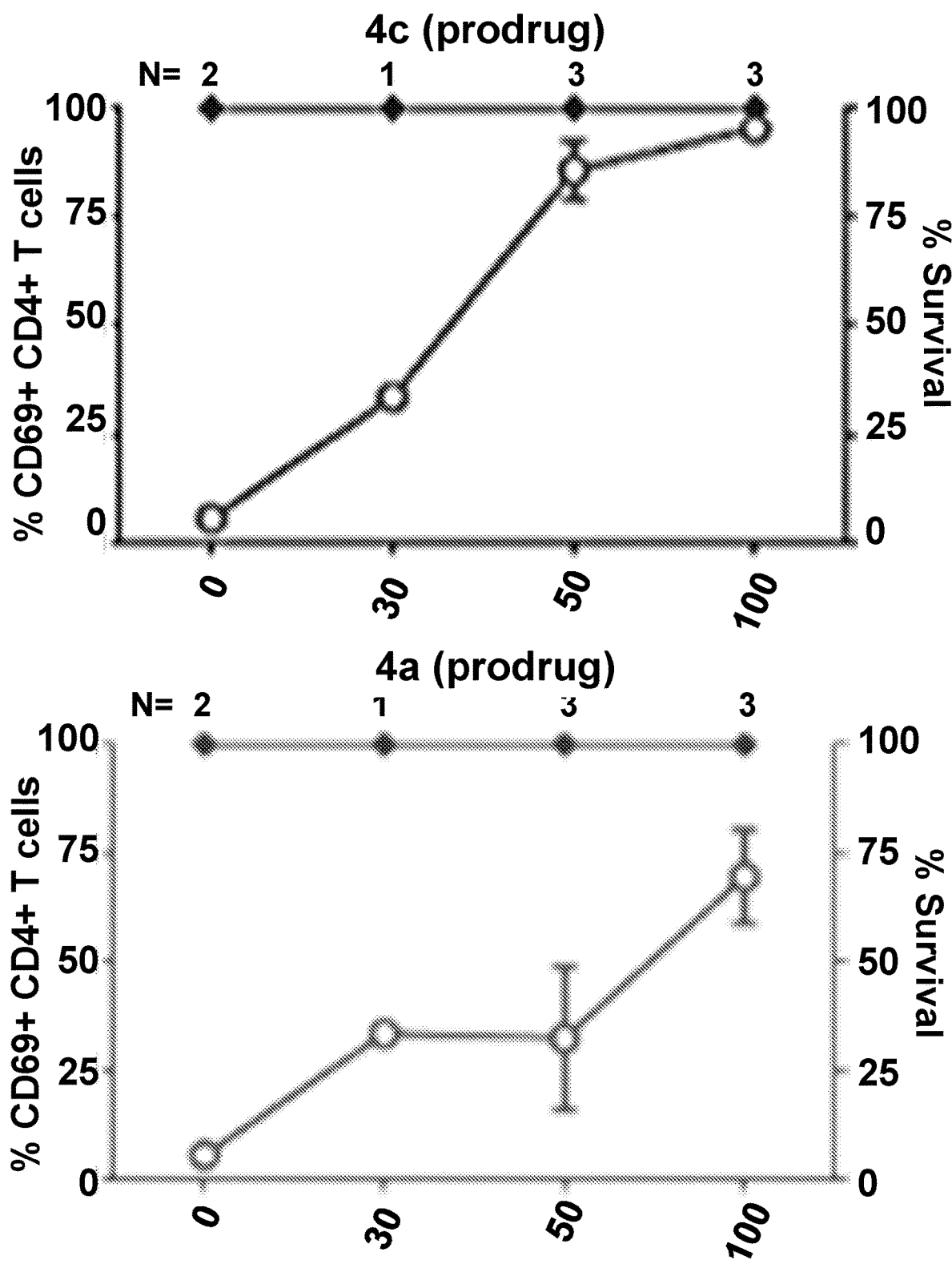
Fig. 7-cont'd

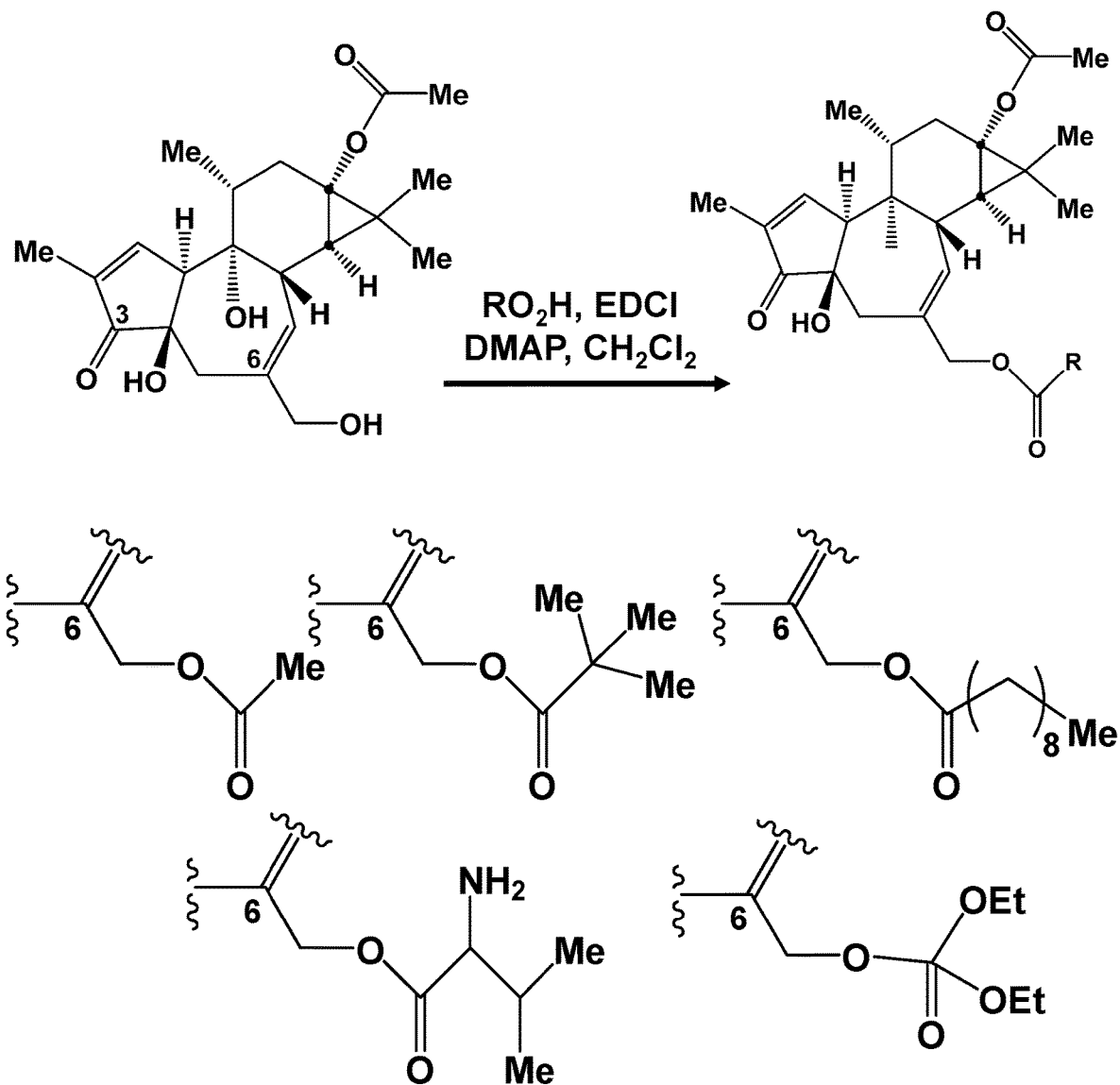
Fig. 11B-cont'd

PRODRUG DERIVATIVES OF PROTEIN KINASE C MODULATORS

CROSS-REFERENCE TO RELATED APPLICATION

This application is the 35 U.S.C. § 371 national stage application of PCT Application No. PCT/US2018/032033, filed May 10, 2018, where the PCT claims priority to U.S. Provisional Application No. 62/505,247, entitled "PRODRUG DERIVATIVES OF PROTEIN KINASE C MODULATORS" filed on May 12, 2017, the entireties of which are herein incorporated by reference.

TECHNICAL FIELD

The present disclosure is generally related to protein kinase C agonist prodrugs. The present disclosure is also generally related to methods of treatment of HIV and other latent virus-related pathologies by administering protein kinase C agonist prodrugs.

BACKGROUND

HIV is a global pandemic, with more than 37 million people currently infected worldwide. Since the start of the HIV epidemic, approximately 39 million have died. Although state-of-the-art antiretroviral therapy (ART) has proven successful in slowing the progression of the disease and lowering plasma viremia, the latent virus persists genetically encoded in reservoir cells. These latently infected CD4$^+$ T cells can survive despite years or even decades of ART. Upon cessation of treatment, even small numbers of latently infected cells can trigger viral replication and a resurgence of the virus. Therefore, patients on ART have to continue therapy for the rest of their lives to prevent return of active virus. This meets with significant cost and compliance problems, with additional risks of side effects from chronic therapy.

Latency reversing agents (LRAs) are considered to be the most promising approach towards providing a cure for HIV/AIDS by reactivating latent reservoir cells. These pharmacological agents can provide a therapeutic effect by inducing viral protein production in resting infected cells, effectively reversing HIV latency. These activated cells can thus become subject to immune-mediated clearance or exogenous cytotoxins capable of targeting active infected cells.

Protein kinase C (PKC) agonists constitute some of the most promising agents for latency reversal, acting by binding PKC in place of its endogenous ligand, diacylglycerol. Ligand binding leads to translocation of PKC to cellular membranes and subsequent signal transduction via phosphorylation of downstream targets. Although researchers have discovered a wide array of PKC agonists, modulation of PKC by some ligands has been demonstrated to activate the canonical NF-κB transcription factor pathway, leading to upregulation of early activation marker CD69, transcription of viral RNA, and thus reactivation of latent viral reservoirs.

For this indication, a number of PKC modulators (e.g. prostratin, ingenanes, bryostatins, and analogs thereof) have been extensively surveyed in vivo, with bryostatin 1 currently in clinical trials for HIV/AIDS eradication (Aphios). In one study, an adamantyl prostratin analog was shown to be 10-fold more potent than prostratin and was also able to activate latent HIV-1 both in vivo and ex vivo (Beans et al., (2013) Proc Natl Acad Sci USA 110, 11698-11703). Additionally, ingenol esters have been reported to activate latent HIV reservoirs at a level that equals or exceeds the current best candidates (Jiang et al., (2014) AIDS 28, 1555-1566).

However, many of the candidate or clinical modulators are difficult to formulate, not optimally effective, and/or exhibit toxicities that individually or collectively limit or preclude their clinical use. The present disclosure encompasses a strategy and rationale for the design and synthesis of prodrugs of PKC modulators, shown to be effective in cells and in live animals. They show significantly increased efficacy and decreased toxicity when compared to the parent compounds and are, therefore, useful for the treatment of the aforementioned diseases. Among various indications, they show high efficacy and improved tolerability as HIV latency reversing agents which could be used in developing a functional cure for HIV/AIDS.

SUMMARY

Embodiments of the present disclosure provide for prodrug derivatives of ingenol, ingenol analogs, prostratin, prostratin analogs, and methods of making, and using said prodrugs.

Accordingly, one aspect of the present disclosure encompasses embodiments of a compound having the formula I:

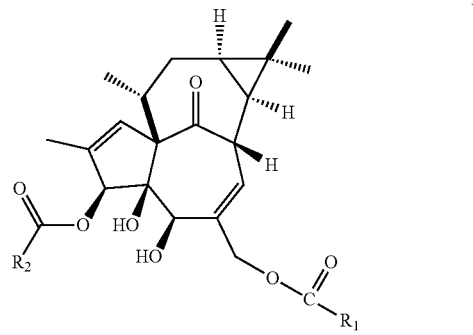

wherein: $R_1$ can be selected from the group consisting of: an alkyl, an aryl, an alkoxy, —NH-alkyl; and $R_2$ can be selected from the group consisting of: a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, $R_1$ is a nonyl ($C_9H_{19}$) group and $R_2$ is para-bromo-ortho-methylphenyl group.

Another aspect of the disclosure encompasses embodiments of a therapeutic composition comprising a protein kinase C (PKC) agonist prodrug in an amount therapeutically effective when delivered to an animal or human subject, wherein the PKC agonist prodrug has the formula I or II:

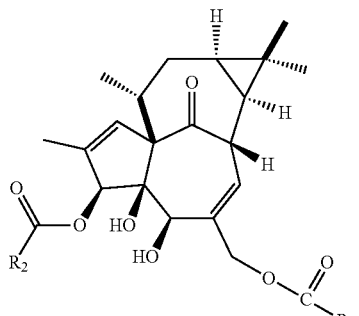

I

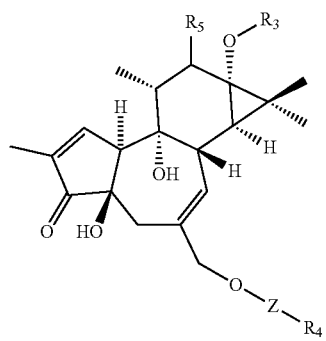

II wherein: Z can be a cleavable linkage; $R_1$ and $R_2$ can be independently selected from the group consisting of: a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl; $R_3$ and $R_5$ are each independently selected from the group consisting of: H, a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl; and $R_4$ can be selected from the group consisting of: a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, the PKC agonist prodrug can have the formula I:

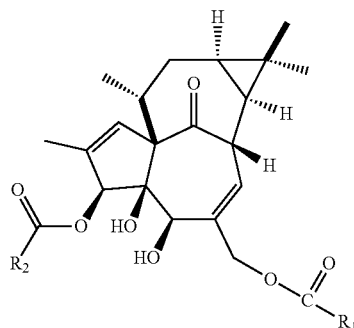

I wherein $R_1$ can be a nonyl ($C_9H_{19}$) group and $R_2$ can be selected from the group consisting of: a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, the PKC agonist prodrug can have the formula I:

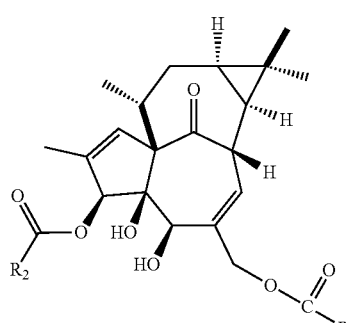

I wherein $R_1$ can be a nonyl ($C_9H_{19}$) group and $R_2$ can be para-bromo-ortho-methylphenyl group.

In some embodiments of this aspect of the disclosure, the PKC agonist prodrug can have formula II and $R_5$ can be H.

In some embodiments of this aspect of the disclosure, $R_3$ is —CO-tricyclo[3.3.1.1$^{3.7}$]decane (—CO-adamantane), and the PKC agonist prodrug has formula:

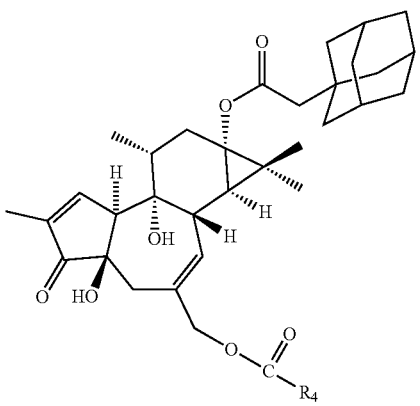

wherein R₄ can be selected from the group consisting of: a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, the PKC agonist prodrug can have the formula II and R₄ can be methyl, pentyl, nonyl, phenyl, ethoxy, or octylamine.

In some embodiments of this aspect of the disclosure, the therapeutic composition can further comprise a pharmaceutically acceptable carrier.

In some embodiments of this aspect of the disclosure, the composition can be formulated for delivery of an effective dose of the protein kinase C (PKC) agonist prodrug to a patient in need thereof intravenously, intraparentally, subcutaneously, intramuscularly, orally, or by inhalation.

Still another aspect of the disclosure encompasses embodiments of a method of modulating the activity of a protein kinase C (PKC) in an animal or human cell comprising contacting an animal or human cell with a pharmaceutically acceptable composition comprising a PKC agonist prodrug having the formula I or II:

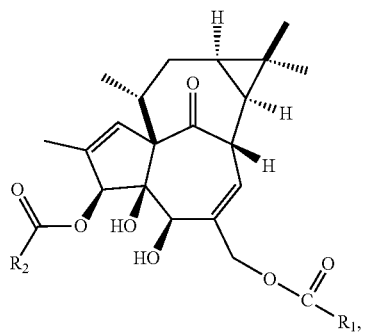

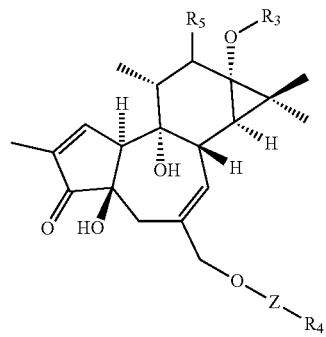

wherein: Z can be a cleavable linkage; R₁ and R₂ can each be selected from the group consisting of: a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl; R₃ and R₅ are each independently selected from the group consisting of: H, a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl; R₄ can be selected from the group consisting of: a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, the PKC agonist prodrug can have the formula I:

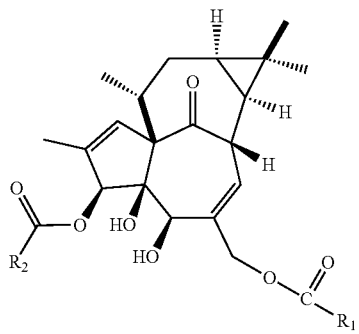

wherein R₁ can be a nonyl (C₉H₁₉) group and R₂ can be selected from the group consisting of: a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, the PKC agonist prodrug has the formula I:

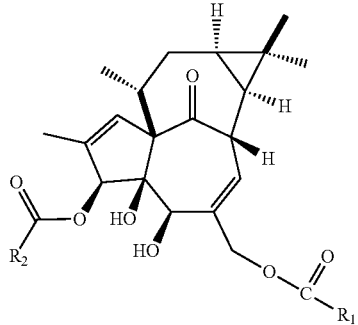

wherein $R_1$ can be a nonyl ($C_9H_{19}$) group and $R_2$ is para-bromo-ortho-methylphenyl group. In some embodiments of this aspect of the disclosure, the PKC agonist prodrug can have formula II and $R_5$ can be H.

In some embodiments of this aspect of the disclosure, $R_1$ is —CO-tricyclo[3.3.1.1$^{3,7}$]decane (—CO-adamantane), and the PKC agonist prodrug has formula:

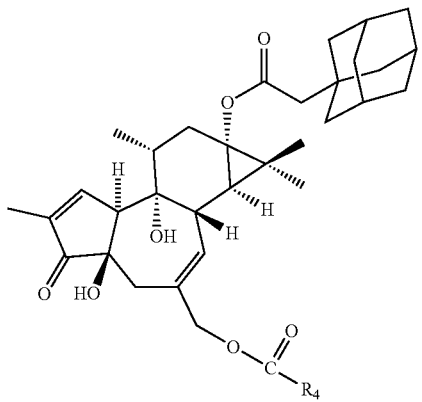

wherein $R_4$ can be selected from the group consisting of: a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, the PKC agonist prodrug can have the formula II and $R_4$ can be methyl, pentyl, nonyl, phenyl, ethoxy, or octylamine.

In some embodiments of this aspect of the disclosure, the pharmaceutically acceptable composition can be administered to an animal or human subject.

In some embodiments of this aspect of the disclosure, the pharmaceutically acceptable composition can be formulated for delivery to a patient in need thereof intravenously, intraparentally, subcutaneously, intramuscularly, orally, or by inhalation.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Figure 1A:
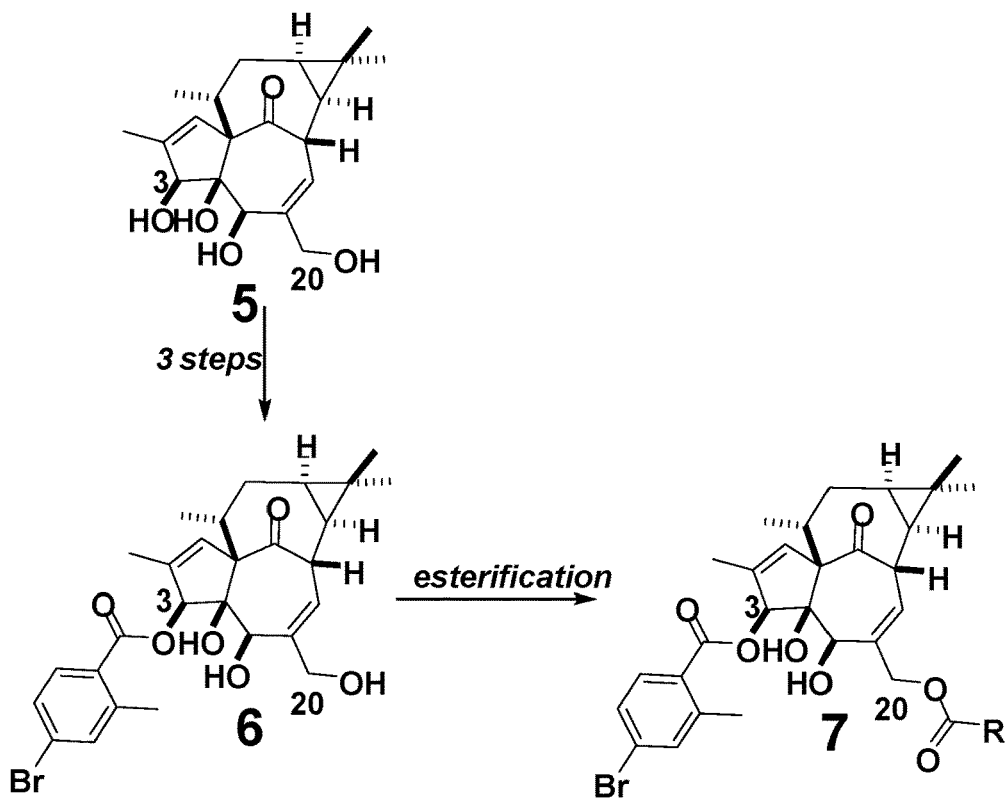
FIG. 1A is a schematic representation illustrating a synthetic method for producing o-methyl-p-bromo-benzoate ingenol ester (6) and corresponding prodrugs (7) from ingenol (5), wherein R corresponds to $R_1$ in Formula I.
Figure 1B:
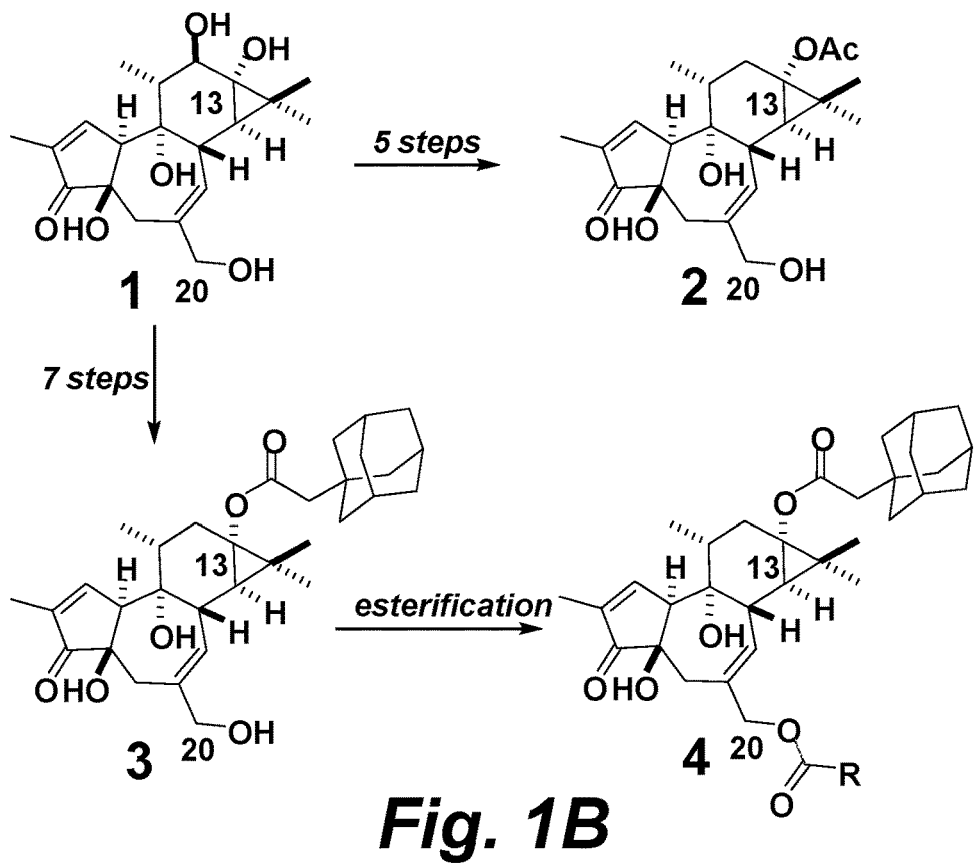
FIG. 1B is a schematic representation illustrating a synthetic method for producing prostratin (2), adamantyl prostratin (3), and corresponding prodrugs (4) from phorbol (1), wherein R corresponds to $R_4$ in Formula II.
Figure 2:
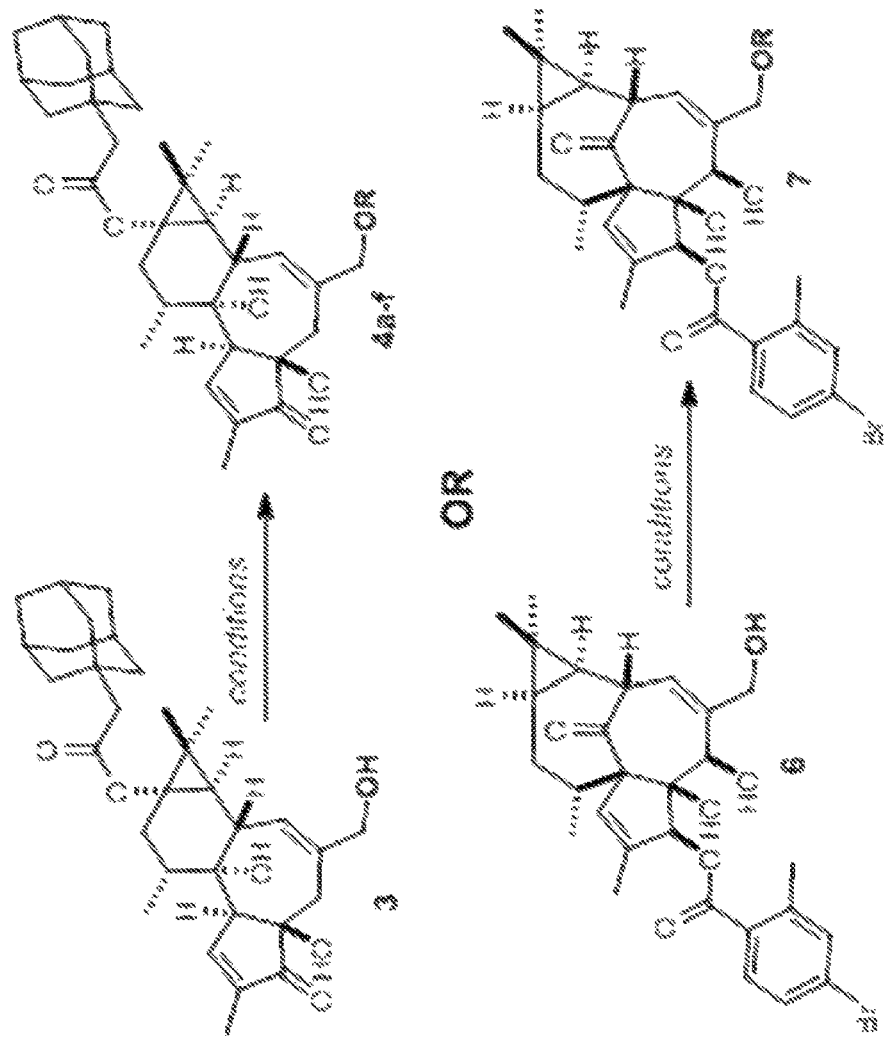
FIG. 2 illustrates structures of prodrugs of the disclosure, showing a schematic representation of $R_1$ substituents in Formula I, where Z is C=O and $R_2$ is p-bromo-o-methylphenyl and certain $R_4$ substituents in Formula II, where Z is C=O, $R_3$ is adamantyl, and $R_3$ is H.
Figure 3A:
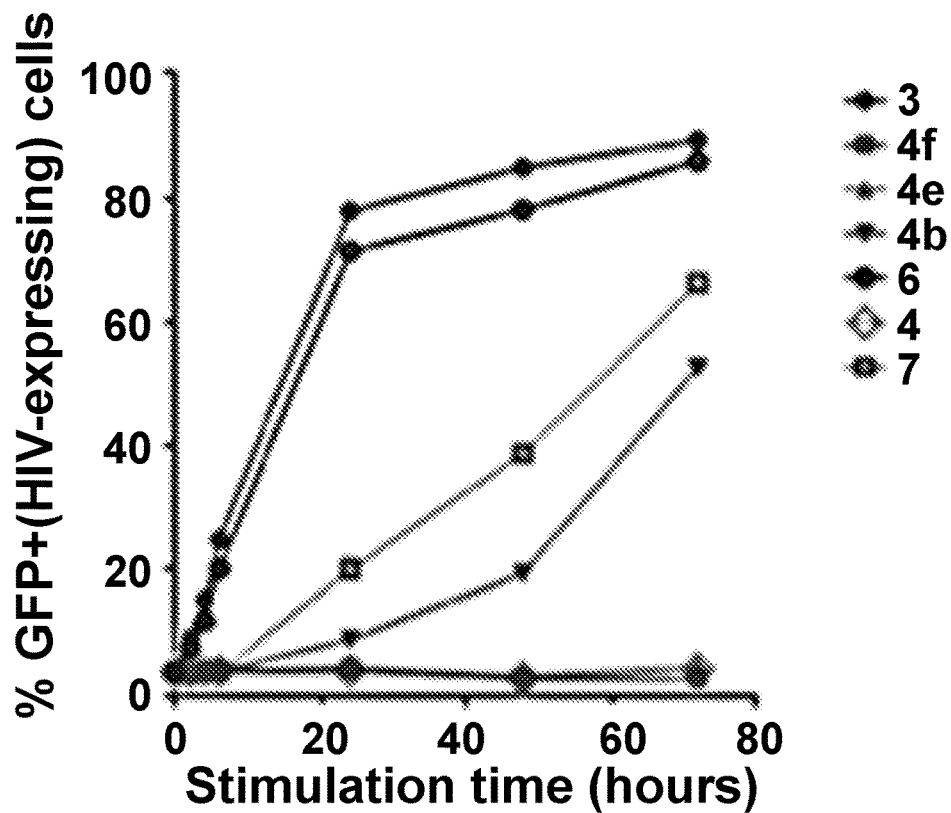
FIGS. 3A-3C illustrate graphs of three experiments that show the induction from latency of HIV in J-Lat 10.6 cell line for prodrug constructs. Mean and SEM of triplicate stimulations are shown for each graph.
Figure 3B:
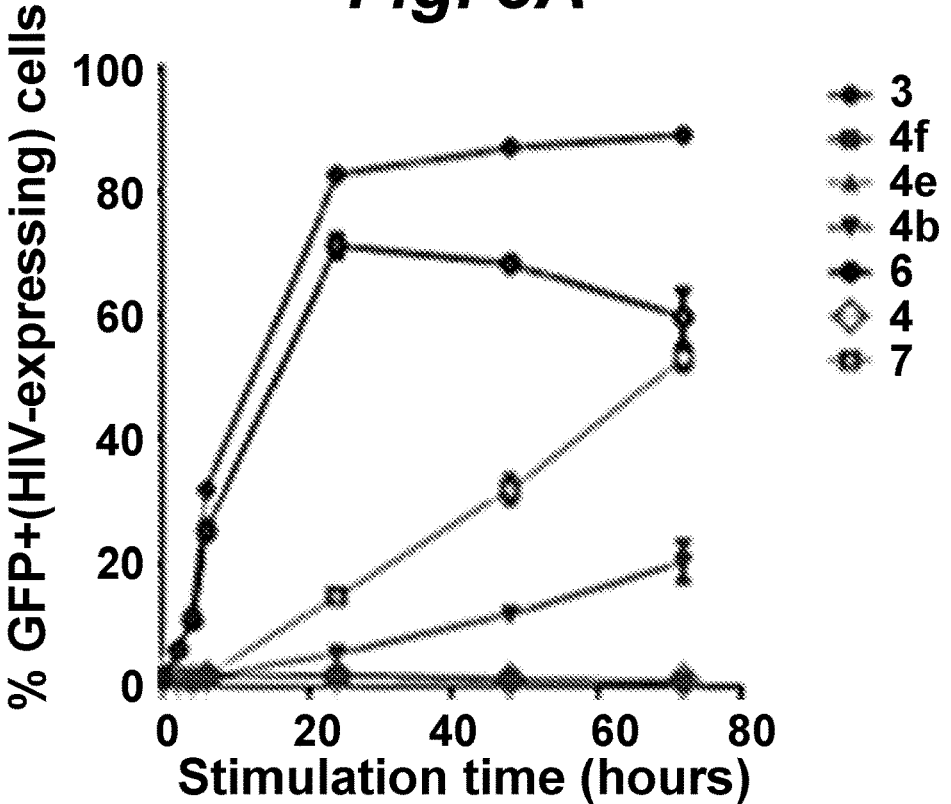
Figure 3C:
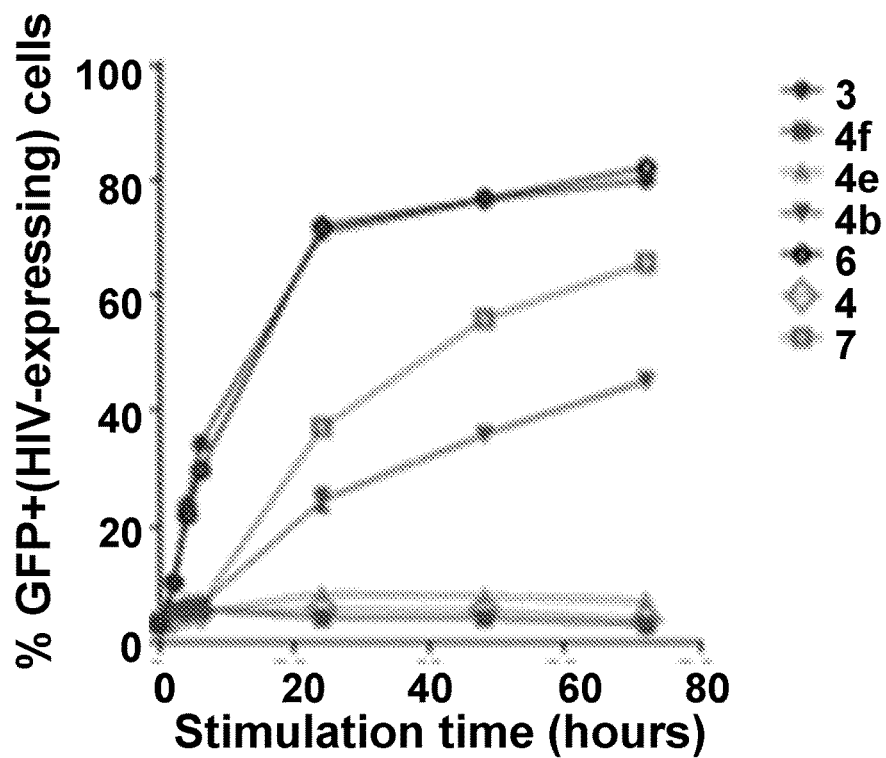
Figure 4:
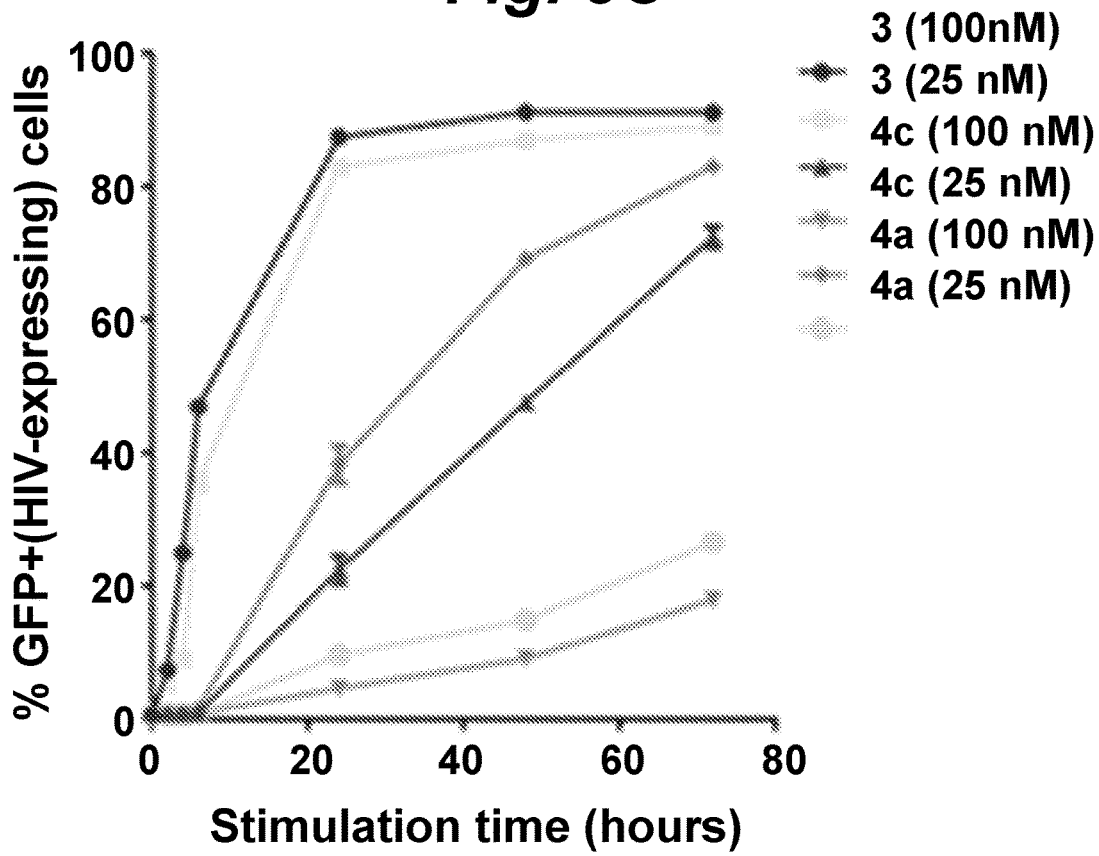
FIG. 4 is a composite graph that shows the induction from latency of HIV in J-Lat 10.6 cell line for varying concentrations of prodrug constructs.
Figure 5A:
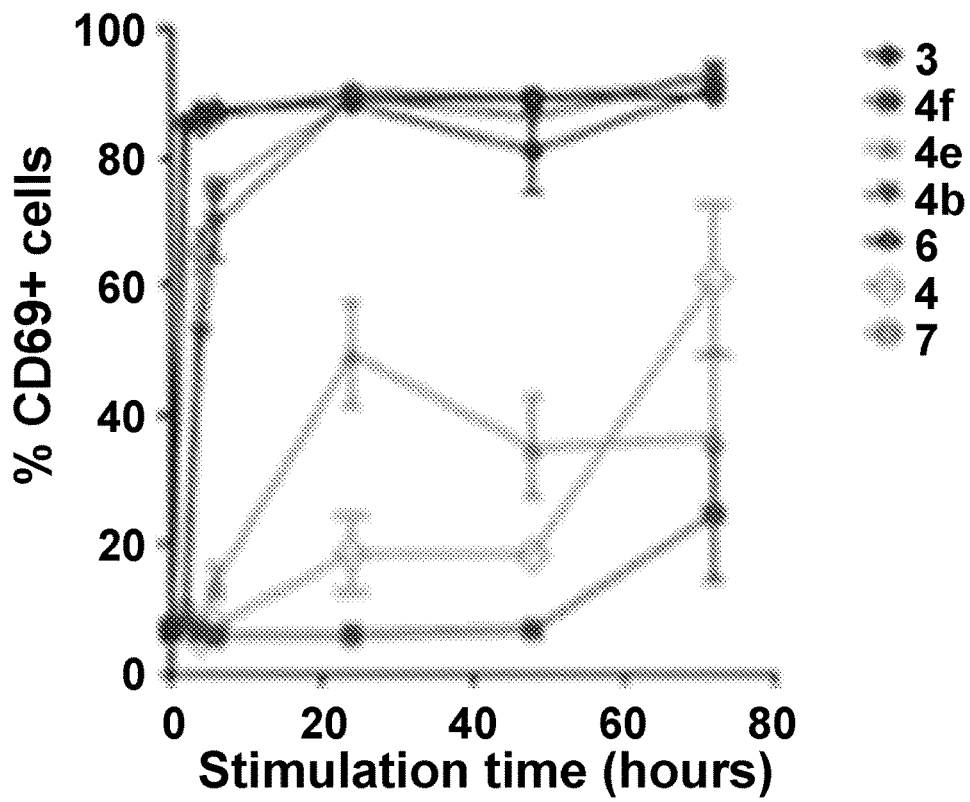
FIGS. 5A-5C illustrate graphs of three experiments that demonstrate the upregulation of CD69 (early biomarker for cell activation that may be correlated with HIV latency reversal) in primary human peripheral blood mononuclear cells (PBMCs) by prodrug constructs. Mean and SEM of triplicate stimulations are shown for each graph.
Figure 5B:
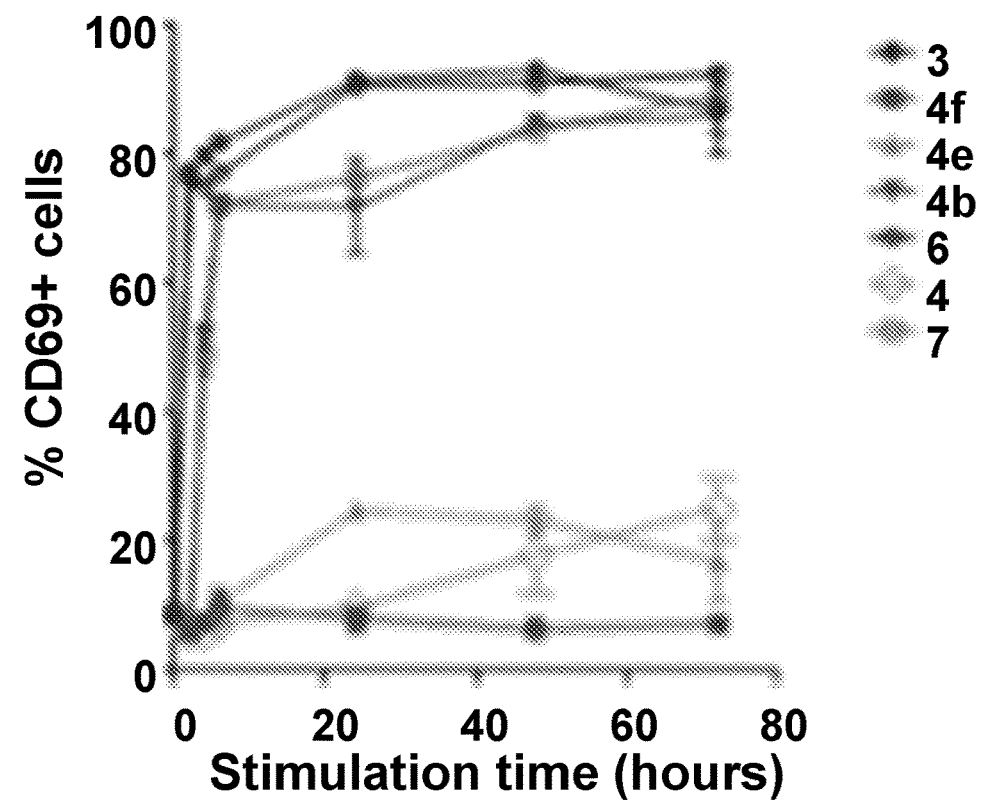
Figure 5C:
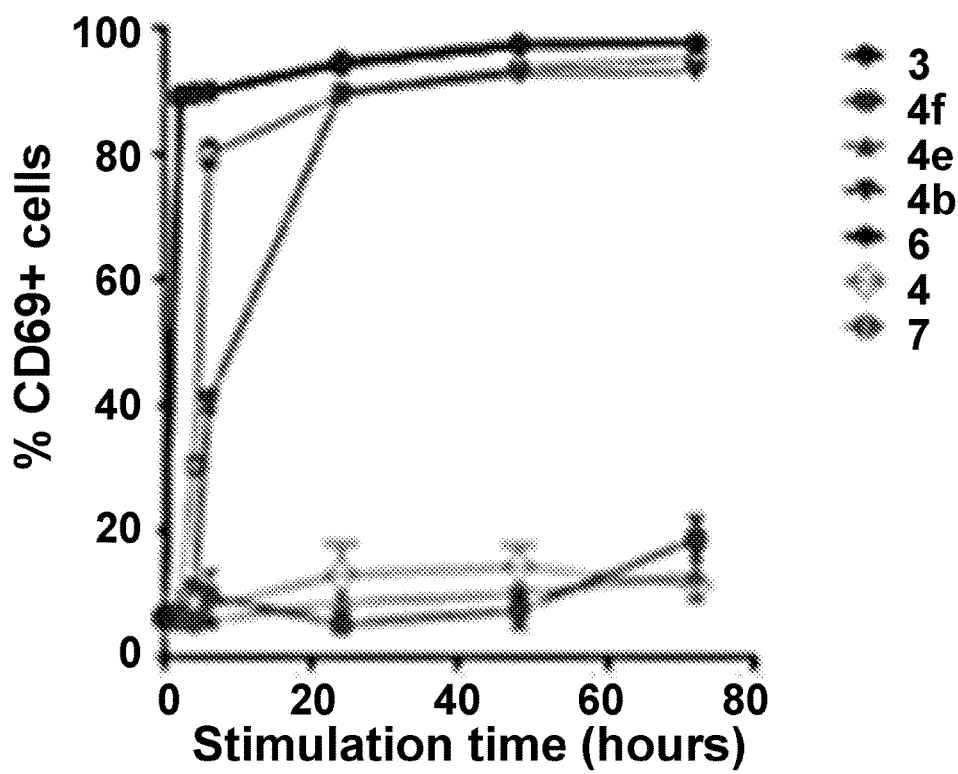
Figure 6:
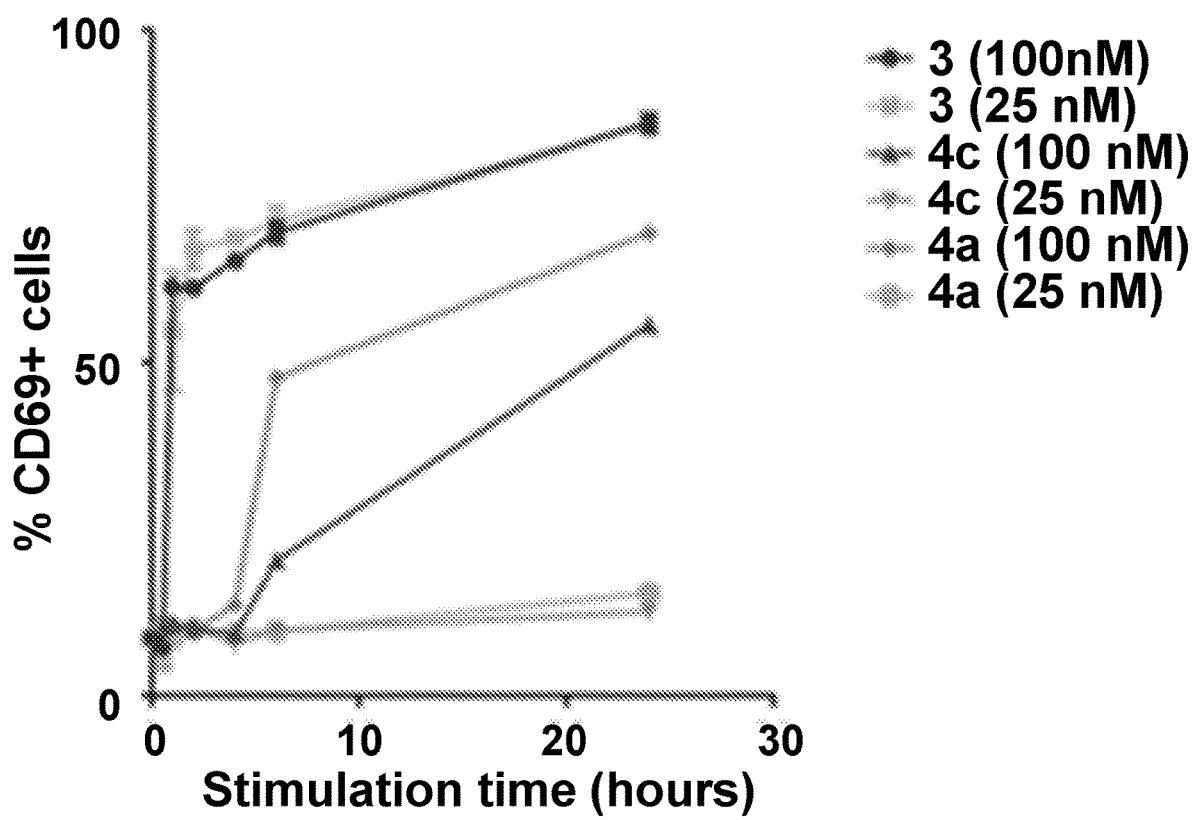
FIG. 6 illustrates a graph that demonstrates the upregulation of CD69 (early biomarker for cell activation that may be correlated with HIV latency reversal) in primary human peripheral blood mononuclear cells (PBMCs) by varying concentrations of prodrug constructs.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, dimensions, frequency ranges, applications, or the like, as such can vary. It is also to be understood that the terminology used herein is for purposes of describing particular embodiments only, and is not intended to be limiting. It is also possible in the present disclosure that steps can be executed in different sequence, where this is logically possible. It is also possible that the embodiments of the present disclosure can be applied to additional embodiments involving measurements beyond the examples described herein, which are not intended to be limiting. It is furthermore possible that the embodiments of the present disclosure can be combined or integrated with other measurement techniques beyond the examples described herein, which are not intended to be limiting.

It should be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

Prior to describing the various embodiments, the following definitions are provided and should be used unless otherwise indicated.

Abbreviations human immunodeficiency virus, HIV; antiretroviral therapy, ART; Latency reversing agent, LRA; histone deacetylase inhibitor, HDACi; protein kinase C, PKC; peripheral blood mononuclear cell, PBMC; highly active antiretroviral therapy, HAART;

Definitions

The term "direct bond" refers to a chemical bond such as a covalent bond or an ionic bond.

The term "substituted" refers to any one or more hydrogens on the designated atom that can be replaced with a selection from the indicated group, provided that the designated atom's normal valence is not exceeded, and that the substitution results in a stable compound. When a substituent is keto (i.e., C—C(=O)—C), then 2 hydrogens on the atom can be replaced. Keto substituents are not present on aromatic moieties. When a ring system (e.g., carbocyclic or heterocyclic) is said to be substituted with a double bond, it is intended that the carbonyl group or double bond be part of the ring.

The term "aliphatic group" refers to a saturated or unsaturated linear or branched hydrocarbon group and encompasses alkyl, alkenyl, and alkynyl groups, for example.

The terms "alkyl" or "alkyl group" as used herein refer to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, s-pentyl, and nonyl. The term "lower alkyl" means an alkyl group having less than 10 carbon atoms.

The terms "alkenyl" or "alkenyl group" as used herein refer to an aliphatic hydrocarbon radical which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "arylalkyl" refers to an arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

The term "substituted," as in "substituted alkyl", "substituted cycloalkyl," "substituted cycloalkenyl," substituted aryl," substituted biaryl," "substituted fused aryl" and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

The terms "halo", "halogen", or "halogen radical" as used herein refer to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

The term "cycloalkyl" refers to a non-aromatic mono-or multicyclic ring system of about 3 to about 10 carbon atoms, preferably of about 5 to about 10 carbon atoms. Advantageous ring sizes of rings of the ring system include about 5 to about 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1-or 2-)yl, tricyclo[3.3.1.1$^{3.7}$]decane, and the like.

The term "cycloalkenyl" refers to a non-aromatic mono- or multicyclic ring system of about 3 to about 10 carbon atoms, preferably of about 5 to about 10 carbon atoms, and which contains at least one carbon-carbon double bond. Advantageous ring sizes of rings of the ring system include about 5 to about 6 ring atoms. Examples of monocyclic cycloalkenyl include cyclopentenyl, cyclohexenyl, cycloheptenyl, and the like. An exemplary multicyclic cycloalkenyl is norbornylenyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl.

The term "biaryl" refers to an aryl, as defined above, where two aryl groups are joined by a direct bond or through an intervening alkyl group, preferably a lower alkyl group.

The term "fused aryl" refers to a multicyclic ring system as included in the term "aryl," and includes aryl groups and heteroaryl groups that are condensed. Examples are naphthyl, anthryl and phenanthryl. The bonds can be attached to any of the rings.

The terms "aralkyl" and "heteroaralkyl" as used herein refer to aryl and heteroaryl moieties, respectively, that are linked to a main structure by an intervening alkyl group, e.g., containing one or more methylene groups.

The term "fluorobenzyl" refers to a benzyl group wherein the phenyl moiety is substituted with one or more fluorine atoms, including 2, 3, 4 and 5 fluorine atom substituents.

Similarly, "halobenzyl" refers to benzyl substituted with one or more different halogens, including fluorine, chlorine, bromine, and iodine (not astatine).

The terms "sulfide" and "thioether" as used herein, alone or in combination, refer to a sulfur atom covalently linked to two atoms; the formal oxidation state of said sulfur is (II). These terms may be used interchangeably.

The term "sulfanyl" as used herein, alone or in combination, refers to the —S—R group, wherein R may be a group such as: alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. Non-limiting examples of sulfanyl groups include methylsulfanyl (—SCH$_3$) and iso-propylsulfanyl (—SCH(CH$_3$)$_2$) and the like.

The term "sulfoxide" as used herein, alone or in combination, refers to a sulfur atom covalently linked to three atoms, at least one of which is an oxygen atom; the formal oxidation state of said sulfur atom is (IV).

The term "sulfinyl" as used herein, alone or in combination, refers to the groups —S(O)—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfinyl group includes methylsulfinyl (—S(O)CH$_3$) and the like.

The term "sulfone" as used herein, alone or in combination, refers to a sulfur atom covalently linked to four atoms, at least two of which are oxygen atoms; the formal oxidation state of said sulfur atom is (VI).

The term "sulfonyl" as used herein, alone or in combination, refers to the groups —S(O$_2$)—R, wherein R may be, but is not limited to alkyl, alkenyl, alkynyl, aryl, alicyclic, heterocyclic, aryl, heteroaryl, arylalkyl and heteroarylalkyl, wherein the alkyl, alkenyl, alkynyl, aryl, alicyclic, heterocyclic, aryl, heteroaryl, arylalkyl and heteroarylalkyl groups may be optionally substituted. A non-limiting example of a sulfonyl group includes methylsulfonyl (—S(O$_2$)CH$_3$) and the like.

The term "phosphine" as used herein, alone or in combination, refers to a phosphorus atom covalently linked to at least one carbon atom, wherein the formal oxidation state of said phosphorus is (III).

The term "phosphinyl" as used herein, alone or in combination, refers to the monoradical derived from a phosphite group, as defined above.

The term "phosphonate" as used herein, alone or in combination, refers to a phosphorus atom covalently linked to four atoms, three of which are oxygen and one of which is carbon wherein the formal oxidation state of said phosphorus is (V).

The term "phosphonyl" as used herein, alone or in combination, refers to the monoradical derived from a phosphonate group, as defined above.

The term "phosphate" as used herein, alone or in combination, refers to a phosphorus atom covalently linked to four oxygen atoms, wherein the formal oxidation state of said phosphorus is (V).

The term "phosphatidyl" as used herein, alone or in combination, refers to the monoradical derived from a phosphate group, as defined above.

The terms ketone, ester, ether, and acyl have their art recognized meanings.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" refers to a compound of the present disclosure that can be modified by making acid or base salts thereof. Pharmaceutically acceptable salt refers to those salts that retain the biological effectiveness and optionally other properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like. Examples of pharmaceutically acceptable salts include, but are not limited to, mineral or organic acid salts of basic residues such as amines; and alkali or organic salts of acidic residues such as carboxylic acids.

In the event that embodiments of the present disclosure form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are advantageous, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

The terms "treat", "treatment", "treating", and the like as used herein refer to acting upon a disease or disorder with an agent to affect the disease or disorder by improving or altering it. The improvement or alteration may include an improvement in symptoms or an alteration in the physiologic pathways associated with the disease or disorder. "Treatment," as used herein, covers one or more treatments of a disease in a host (e.g., a mammal, typically a human or non-human animal of veterinary interest), and includes: (a) reducing the risk of occurrence of the disease in a subject determined to be predisposed to the disease but not yet diagnosed as infected with the disease (HIV/AIDS) (b) impeding the development of the disease, and/or (c) relieving the disease, e.g., causing regression of the disease and/or relieving one or more disease symptoms.

The terms "prophylactically treat" or "prophylactically treating" as used herein refer completely or partially preventing (e.g., about 50% or more, about 60% or more, about 70% or more, about 80% or more, about 90% or more, about 95% or more, or about 99% or more) a disease or symptom thereof and/or may be therapeutic in terms of a partial or complete cure for a disease and/or adverse effect attributable to the disease.

The terms "activate" and "activation" can refer to a response (e.g., immune response) from acting upon a biological target with a compound of the present disclosure.

The terms "agent", "active agent", or the like, as used herein refer to a compound of the present disclosure. The agent or inhibitor can be disposed in a composition or a pharmaceutical composition.

The term "pharmaceutical composition" as used herein refers to the combination of an active agent with a pharmaceutically acceptable carrier. As used herein, a "pharmaceutical composition" refers to a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The terms "pharmaceutically acceptable excipient," "pharmaceutically acceptable diluent," "pharmaceutically acceptable carrier," or "pharmaceutically acceptable adjuvant" as used herein refer to an excipient, diluent, or carrier that is useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, or carrier" as used in the specification and claims includes one or more such excipients, diluents, and carriers.

The term "isolated compound" refers to a compound which has been substantially separated from, or enriched relative to, other compounds with which it occurs in nature. Isolated compounds are usually at least about 80% pure, at least 90% pure, at least 98% pure, or at least about 99% pure, by weight. The present disclosure is meant to include diastereomers as well as their racemic and resolved, enantiomerically pure forms and pharmaceutically acceptable salts thereof.

The term "unit dosage form," as used herein, refers to physically discrete units suitable as unitary dosages for human and/or animal subjects, each unit containing a predetermined quantity of a compound calculated in an amount sufficient (e.g., weight of host, disease, severity of the disease, etc.) to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

The term "therapeutic (or pharmaceutical) composition" as used herein refers to a composition that includes a therapeutically effective compound at a level sufficient to induce a desired biological result. That result may be the alleviation of the signs, symptoms or causes of a disease or any other alteration of a biological system that is desired.

The term "therapeutic ally effective amount" as used herein refers to an amount of therapeutic compound that is effective, at dosages and for periods of time necessary, to achieve the desired therapeutic or prophylactic result. A "therapeutically effective amount" of a therapeutic compound may vary according to factors such as the disease state, age, sex, and weight of the individual. A therapeutically effective amount may be measured, for example, by improved survival rate, more rapid recovery, or amelioration, improvement or elimination of symptoms, or other acceptable biomarkers or surrogate markers. A therapeutically effective amount is also one in which any toxic or detrimental effects of the therapeutic compound are outweighed by the therapeutically beneficial effects. A "prophylactically effective amount" refers to an amount of therapeutic compound that is effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. Furthermore, therapeutically effective amounts will vary, as recognized by those skilled in the art, depending on the specific disease treated, the route of administration, the excipient selected, and the possibility of combination therapy. A physiological effect of a compound as disclosed herein on the subject can be measured to determine the therapeutically effective amount includes, without limitation, decreased proliferation in a subject and the like.

The term "prostratin" as used herein refers to a nontumor-promoting 12-deoxyphorbol ester (IUPAC name: 1aR,1bS,4aR,7aS,7bR,8R,9aS)-4a,7b-dihydroxy-3-(hydroxymethyl)-1,1,6,8-tetramethyl-5-oxo-1,1a,1b,4,4a,5,7a,7b,8,9-decahydro-9aH-cyclopropa[3,4]benzo[1,2-e]azulen-9a-ylacetate) that has been shown to inhibit HIV-induced cell death and viral replication in vitro. The antiviral activity of this compound was discovered as a result of ethnobotanical studies on the island of Savai'i, Samoa, where traditional healers use the bark of *Homalanthus nutans* (G. Forst.) Guill. (Euphorbiaceae), a small rain-forest tree called "mamala", to treat hepatitis. Low concentrations of prostratin, from 0.1 to >25 μM, have been found to protect T-lymphoblastoid CEM-SS and C-8166 cells from the lethal effects of HIV-1 and inhibit viral replication in these cell lines. The compound also demonstrated cytoprotective activity in the human monocytic cell line U937 and in freshly isolated human monocyte/macrophage cultures. Prostratin was found to bind to and activate protein kinase C in vitro in CEM-SS cells. Unlike other known phorbol esters, however, the compound has proved not to be a tumor promoter and has actually been shown to be a potent antitumor promoter. Examples of prostratin, and derivatives and prodrugs thereof suitable for inclusion in the pharmaceutical compositions of the disclosure are given, for example, in U.S. Pat. Ser. No. 8,816,122.

In latently infected $CD4^+$ T cells, prostratin induces HIV gene expression. NF-κB and PKC (α and θ) activation are the key events triggered by prostratin. Although other phorbol esters such as PMA (phorbol 12-myristate-13-acetate) are also shown to activate latent HIV, prostratin differs markedly from these and offers distinct therapeutic value because it does not exhibit the tumor-promoting activity of these other agents. Therefore, prostratin is a promising therapeutic lead as an adjuvant to be used in HAART (highly active antiretroviral therapy).

In an in vitro study, prostratin was shown to protect T-lymphoblastoid CEM-SS and C-8166 cell lines. At a prostratin concentration of approximately 1 μM, cell viability was restored to the level of uninfected controls, and no sign of cytotoxicity was observed up to about 25 μM. The mode of action is unclear, but the Ki of prostratin for PKC is 12 nM, suggesting the involvement of PKC in the process. (Gulakowski et al., (1997) *Antiviral Res.* 33: 87-97). Prostratin also inhibits HIV invasion into healthy cells by down-regulating the expression of HIV receptors on cell surfaces.

The term "prodrug" refers to a compound whose efficacy may be enhanced after a conversion step that occurs in vivo after administering the compound to a subject or patient.

The term "pharmaceutically acceptable prodrugs" refers to those prodrugs of the compounds useful according to the present disclosure which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the disclosure. Exemplar prodrugs are described below in reference to prostratin and bryostatin and their analogs. Functional groups that may be rapidly transformed, by in vivo metabolic cleavage, to form a class of groups reactive with the carboxyl group of the compounds of this disclosure. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl-and triethysilyl), monoesters formed with dicarboxylic acids (such as succinyl), and the like. Because of the ease with which the metabolically cleavable groups of the compounds useful according to this disclosure are cleaved in vivo, the compounds bearing such groups act as pro-drugs. The compounds bearing the metabolically cleavable groups have the advantage that they may exhibit improved bioavailability and or better ease of administration as a result of enhanced solubility and/or rate of absorption conferred upon the parent compound by virtue of the presence of the metabolically cleavable group. Prodrugs can include compounds of the present disclosure wherein a hydroxy, amino, or sulfhydryl group is bonded to any group that, when the prodrug of the present disclosure is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present disclosure. Additional examples are described in detail with relation to prostratin, ingenol, and their analogs.

To the extent that the disclosed compounds, and salts thereof, may exist in their tautomeric form, all such tautomeric forms are contemplated herein as part of the present disclosure.

All stereoisomers of the compounds of the present disclosure, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "administration" as used herein refers to introducing a compound of the present disclosure into a host. One advantageous route of administration of the compound is oral administration. Another advantageous route is intravenous administration. However, any route of administration, such as topical, subcutaneous, peritoneal, intraarterial, inhalation, vaginal, rectal, nasal, introduction into the cerebrospinal fluid, or instillation into body compartments can be used.

The terms "host," "subject," "patient," or "organism" as used herein, include humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

Discussion

Protein kinase C (PKC) modulators are candidates for the therapeutic treatment of a variety of major diseases. Some PKC modulators are in clinical trials for Alzheimer's disease (AD), HIV/AIDS eradication, and cancer. However, these highly potent PKC modulators are also difficult to formulate, display non-optimal efficacy as drugs, and possess unacceptable toxicities. Administration of these compounds often elicits acute toxicities due to bolus effects arising from the high concentration of agent at the site of administration or systemically. This bolus toxicity can be decreased by slow administration, but this adds complications to both preclinical animal studies and the clinical use of these compounds. For example, the highly potent PKC modulator bryostatin 1 is administered over 24 hours via intravenous injection of a diluted saline solution. In other cases, toxicities arrive from the undesired biodistribution of the compound which is determined by the properties of the compound. The combination of formulation problems, bolus toxicity, toxicities arising from undesired biodistribution, and efficacy severely reduces the therapeutic window for such compounds. Additionally, many PKC modulators suffer from stability problems, undergoing adventitious aerobic or metabolic oxidation. This compromises their shelf stability before administration and limits their lifetime during circulation in a patient after administration. While the properties of many PKC modulators can be improved to combat stability problems, often that improvement is accompanied by higher toxicities or lower efficacies. In contrast to bolus administration which provides short-lived but high exposure to the modulator, controlled release of free agent from a modified precursor (prodrug) allows for sustained release of the modulator at optimal concentrations for extended periods (Rautio et al., (2008), *Nat. Rev. Drug. Discov.* 7: 255). This offers improved efficacy and tolerability.

The reversible attaching of a masking group to one of these functional elements results in compounds that have altered properties and are temporarily ineffective as PKC modulators until the free agent is released by enzymatic or abiological cleavage in vivo (Ettmayer et al., (2004) *J. Med. Chem.* 47:2393; Liederer & Borchardt (2006) *Pharm. Sci.* 95: 1177). These compounds display rates of release and biodistribution that can be tuned and controlled by design. Specifically, it has now been demonstrated that these compounds have delayed activity profiles in an HIV latency reversal assay (t½=24-72 h) versus the parent compound (t½ less than 24 h), but limited toxicity (mouse kill at 150 μg for the prodrugs, versus 60 μg for the parent compound). Additionally, the prodrugs of the disclosure display improved efficacy over the parent compound at comparable doses (nearly 100% cell activation by a prodrug versus 60-80% by the parent compound).

Accordingly, provided is a strategy for the design of prodrugs of PKC modulators that show efficacy coupled with low levels of toxicity and improved stability. These prodrug compounds are useful in academic research (animal studies), as candidates for preclinical research, and as therapeutic agents. By taking advantage of a pharmacophore-based strategy, this method provides access to prodrugs of PKC modulators of diverse scaffolds, including, but not limited to tigliane diterpenes, ingenane diterpenes, daphnane diterpene orthoesters (DDOs), diacylglycerols (DAGs), and bryostatins.

Embodiments of the present disclosure provide for prodrug derivatives of PKC modulators including, but not limited to ingenol analogs, prostratin analogs, bryostatin analogs, methods of making such prodrugs of ingenol, prostratin, and bryostatin analogs, and methods of their therapeutic use.

In particular, embodiments of the present disclosure provide for prodrug ingenane esters having substitutions at C20 (Formula I).

Figure 8:
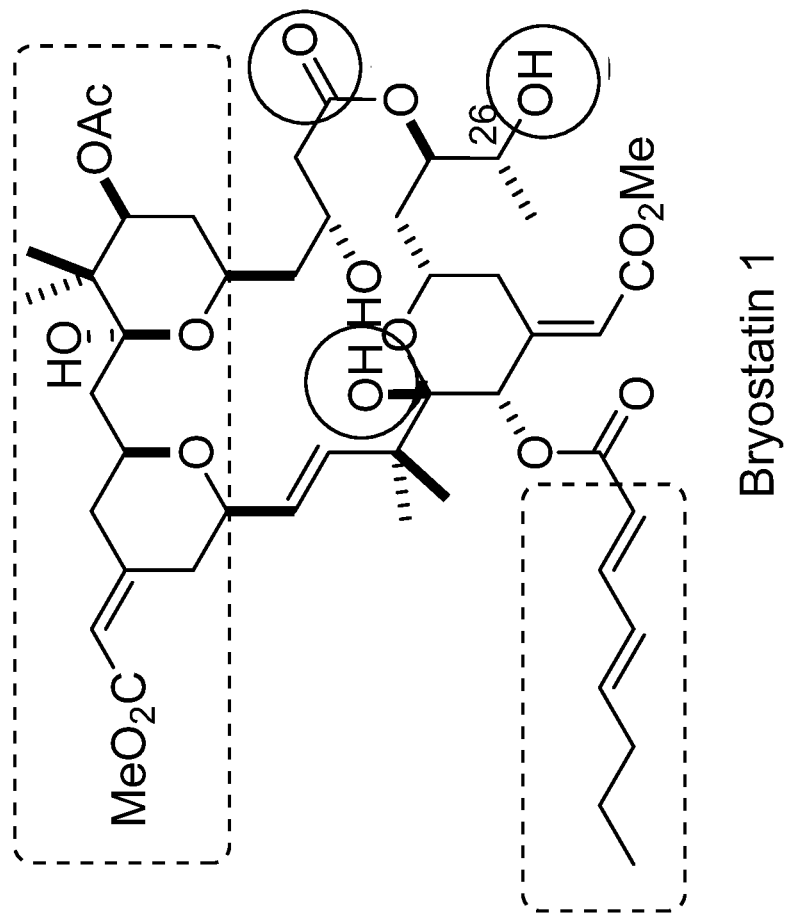
FIG. 8 illustrates embodiments of pharmacophores of PKC modulators. Circled elements represent pharmacophoric hydrogen bond donors/acceptors. Dashed boxes encompass hydrophobic regions.
Figure 8:
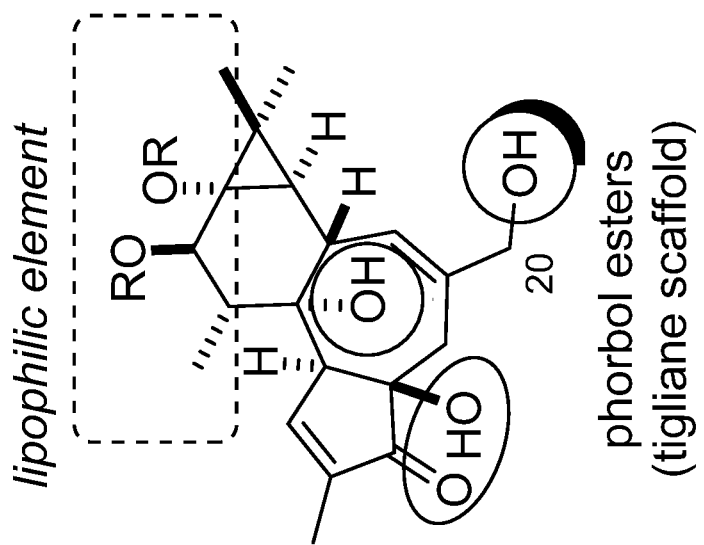

Embodiments of the pharmaceutically acceptable prodrugs of the disclosure can exhibit activity against human immunodeficiency virus (HIV), stimulate transcription of proviral HIV DNA, and/or bind to protein kinase C. It has been discovered that prostratin, ingenol, and bryostatin analogs have a common pharmacophore as shown in FIG. 8 (i.e., same or similar subset of groups responsible for biological activity), and consequently have similar activities.

Parent PKC modulators of the present disclosure have been used as protective adjuvants in anticancer radiotherapy. Activators of NF-κB pathway can protect healthy cells from the radiation during anticancer radiotherapy. In studies with mice and rhesus monkeys, the survival rate of the animals after radiation therapy was significantly improved when the NF-κB activators were injected to the animals (*Science*, 2008, 320, 226-230, which is incorporated herein by reference).

The ring numbering in ingenol and analogs thereof as follows:

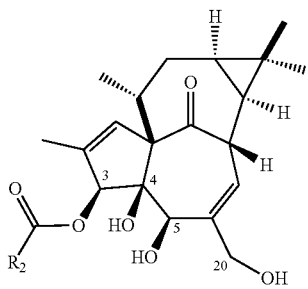

is provided for convenience and is also as found in US Application No. 2015/0291551.

The ring numbering in prostratin and analogs thereof as follows:

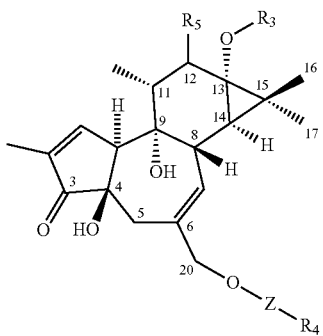

is provided for convenience and is also as found in U.S. Pat. No. 5,599,839. It is also understood that prostratin and derivatives thereof comprise four rings denominated from left to right A, (including position 3), B (including position 6), C (including position 12), and D (including position 15). The stereochemistry indicated above represents an advantageous embodiment. By way of illustration in prostratin, $R_3$ is H, X is O, $R_1$ is —C(=O)CH$_3$, and $R_2$ is H. Another known compound, DPP, is similar except that $R_1$ is C(=O)CH$_2$Phenyl. Another known compound, TPP (See U.S. Patent Application 2008/0226589) is similar except that $R_1$ is C(=O)C$_{13}$H$_{27}$.

Compounds having novel substituents at positions C12 ($R_5$ in the formula above) and C13 (X—$R_1$ in the formula above) are described and are termed herein C12 or C13 analogs. Also described in connection with the present disclosure are prodrugs of prostratin, or of novel compounds having different chemical groups at the C20 position (XR$_4$ in the formula above).

In an embodiment, the present disclosure involves modifications in the prostratin/DPP structure at C13 that can provide improved binding to protein kinase C (PKC), and certain PKC isozymes. Examples of the present analogs have been shown to be more potent than prostratin. For example, C13 can contain a carbonyl group and a fused, modified aromatic structure, FMA, as represented where, in the above formula, $R_3$ is —C(=O)-FMA, or —C(=O)CH$_2$-FMA, or —C(=O)CH(CH$_3$)-FMA, where FMA may be, for example, a group derived from benzene, naphthalene, azulene, phenanthrene, anthracene, pyridine, quinoline, isoquinoline, purine, pyrimidine, pyrrole, indole, carbazole, furan, thiophene, imidazole, isoxazole, thiazole or their substituted or benzo derivatives. Various substitutions in the fused modified aromatic structure are possible and are described herein. Also described herein are compounds where $R_3$ is a cycloalkyl or other alkyl. Other linear, branched or cyclic alkanes may also be used as attached groups, such as bridged or spiro hydrocarbons, e.g., tricycle[3.3.1.1] decane (adamantane).

In another embodiment, the present disclosure comprises C20 prodrugs of C12 analogs. The term "C12 analog" refers to a compound that is not H in its C12 position as shown in the above formula. These methods begin with phorbol. Methods of synthesis can be as described in U.S. Pat. No. 8,816,122, incorporated herein by reference in its entirety. The C13 hydroxyl is esterified after the C20 hydroxy is protected. This permits reactions with the C12 hydroxyl group, such as alkylation. Alkylation reactions with cycloalcohol may be used to produce alkyl ethers.

In embodiments pertaining to C13 analogs, $R_5$ is H, otherwise $R_5$ is as defined below. X in each instance is independently selected from O, S, C, and N, most advantageously O.

Figure 9:
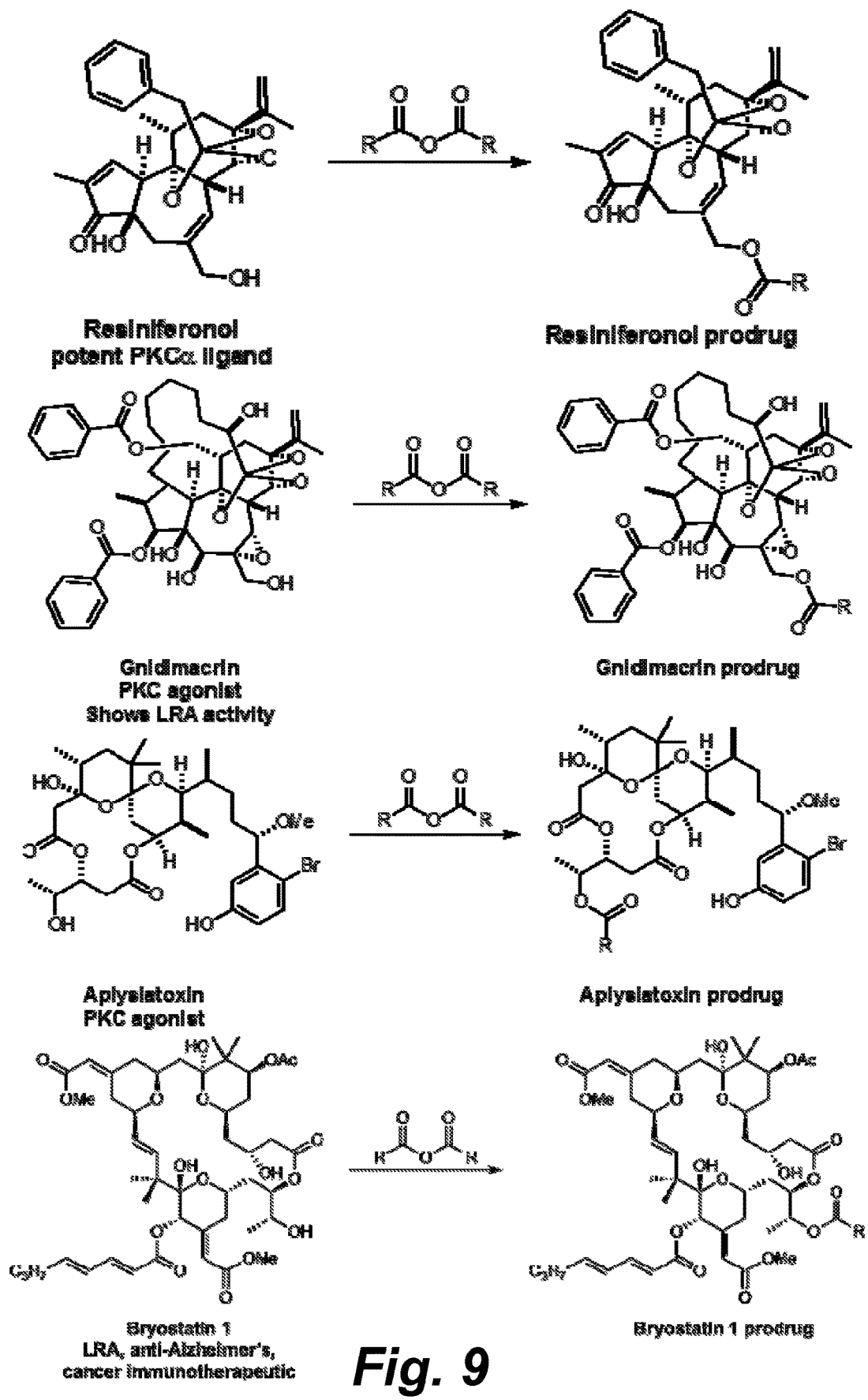
FIG. 9 illustrates embodiments of prodrugs of the disclosure.
Figure 10:
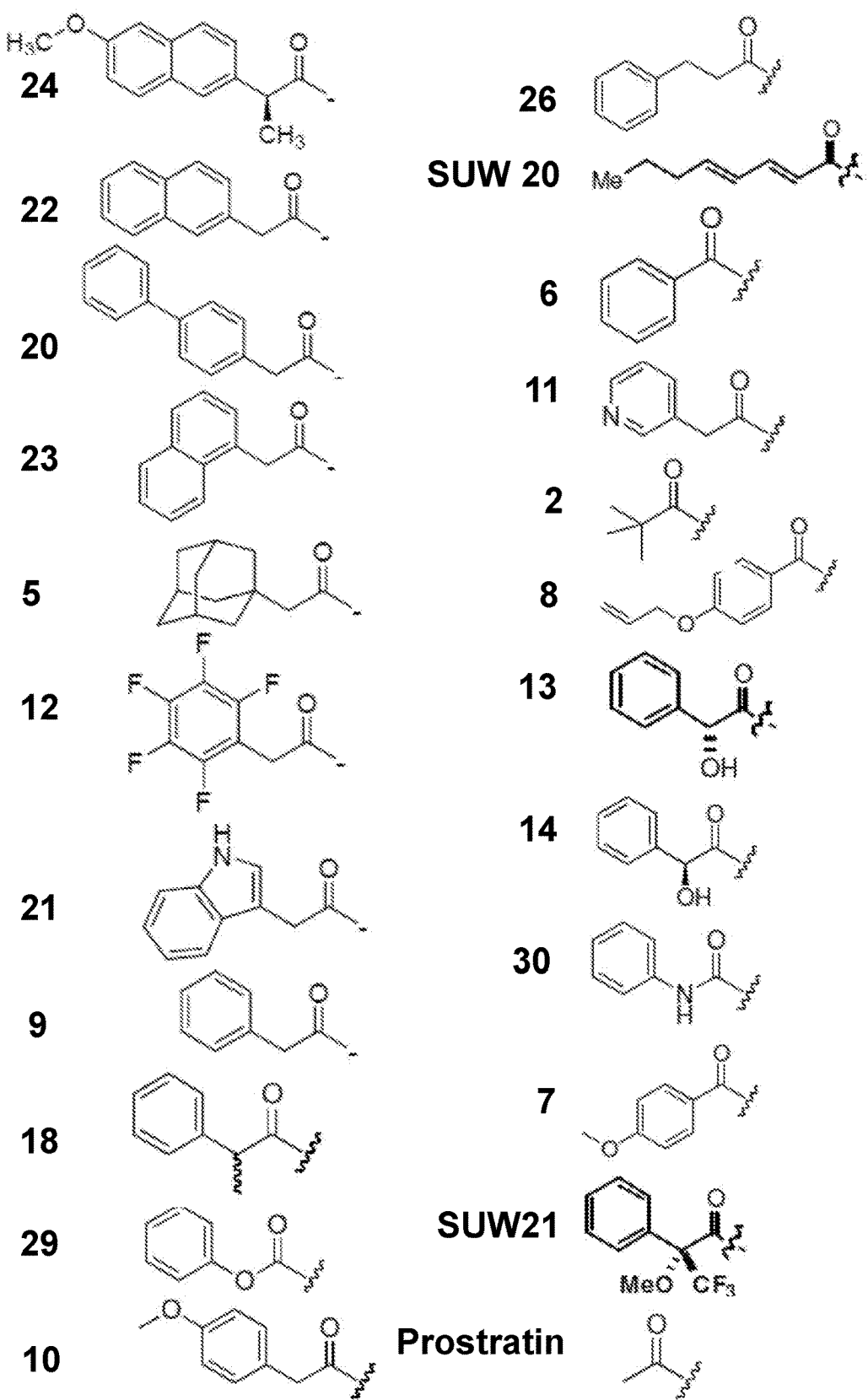
FIG. 10 illustrates schematic representations of certain prostratin $R_1$ substituents, where X=O, $R_2$=H, and $R_3$=H. Embodiments of present compounds are listed in order as compounds 24, 22, 20, 23, 5, 12, 21, 9, 18, 4, 29, 10, 26, SUW 20, 3, 6, 11, 2, 8, 13, 14, 30, 7 and SUW21.

$R_3$, relating to C13 analogs, can be selected from a mono-or di-substituent, depending on X, selected from: H, substituted or unsubstituted alkyl, substituted or unsubstituted aryl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl. In particular, $R_1$ may be selected from: aryl, biaryl, fused aryl, branched alkyl, or cycloalkyl groups, as well as phosphates, sulfates, and the like, as well as esters and related or similar groups that can be linked to X and have substituents selected from: aryl, biaryl, fused aryl, branched alkyl, or cycloalkyl groups including bridged or spiro hydrocarbons, e.g., tricycle [3.3.1.1] decane. (adamantane). Representative $R_3$ groups are shown, for example, in FIG. 9.

$R_4$, at the C20 position, may be varied independently of $R_3$ or $R_5$, or may be H. In an embodiment, $R_4$ can be selected from: a mono-or di-substituent selected from H or a prodrug linkage which is selected from: an acyl, disulfide, amido, ester, primary or secondary amine, hydroxyl, sulfhydryl, carboxyl, aldehyde, ketone, bromide, fluoride, and chloride. $R_4$ may be H or a prodrug linkage such as an acyl, disulfide, amido, or ester. In an embodiment, the reactive functional groups include primary or secondary amines, hydroxyls, sulfhydryls, carboxyls, aldehydes, and ketones, bromides, fluorides, and chlorides. In an embodiment, the reactive functional groups include disulfide and esters.

$R_5$, at the C12 position, may be varied independently of $R_3$ and $R_4$. In an embodiment, $R_5$ can be a substituent selected from: H, substituted or unsubstituted alkyl, substituted or unsubstituted aralkyl, substituted or unsubstituted cycloalkyl, substituted or unsubstituted cycloalkenyl, substituted or unsubstituted aryl, substituted or unsubstituted biaryl, substituted or unsubstituted fused aryl, substituted or unsubstituted alkenyl, and substituted or unsubstituted alkynyl. In an embodiment, $R_5$ can be selected from: methoxy, ethoxy, acetoxy, acyloxy, phenyloxy, methylthio, ethylthio, phenylthio, fluoro, chloro, bromo, diethylamino, diphenylamino, dimethylamino, keto, methyl, ethyl, methylene, but not limited to, exocyclic olefin similar to C12=CH$_2$ or ethylene C12=CH—CH$_3$. Analogs of phorbol esters, such as 12-deoxy phorbol esters, are disclosed where the C13 substituent has been modified from the C13 structure found in prostratin. The analogs differ significantly from the structure of prostratin, e.g., where C13 is —O—C(=O)—CH$_3$ and also differ significantly from 12-deoxyphorbol 13-phenylacetate (DPP), i.e., —O—C(=O)—C-Ph, where Ph is phenyl. As represented in the formula above R$_3$ may be a variety of aryl, biaryl, fused aryl, branched alkyl or cycloalkyl groups. Advantageous R$_3$ compounds are hydrogen bond donors or acceptors.

Most specifically, the present disclosure relates to prodrugs of tiglane and ingenane diterpene compounds. The prodrugs employ a modification at the C20 position, in combination with possible modifications at C3, C12, and C13 as described herein, whereby a cleavable linkage is used to create a labile bond at the C20 position that will yield a hydroxyl group upon activation. The linkage is from the C20 carbon to another group such as, for example, an ester, which is metabolized in vivo to produce a C20 hydroxyl group. The inactive group may be selected to enhance cellular uptake, such as an oligopeptide having a positive charge, which facilitates penetration of the drug into the cellular membrane, as described, for example in U.S. Pat. Nos. 7,585,834, 7,939,621, 8,792,010, and 8,795,734. Embodiments of the present disclosure include prodrugs of any of the above prostratin analogs.

The prodrugs of the disclosure have the general formula PKC-C20-linkage-CU, where PKC is a protein kinase C modulator such as prostratin or a prostratin analog, ingenol or ingenol analog, C20 is the C20 carbon in that structure, linkage is a cleavable linkage, and CU is an organic group or other group (e.g., phosphate-based) that may be inert or confer stability, but preferably enhances uptake or activation of the PKC or provides a method for slow release of the active drug in vivo. For example, the C20 position of prostratin (or any other analog described herein) can be acylated rendering it inactive. Under treatment conditions this acyl group would be cleaved either chemically or biologically (e.g., esterases) to release free prostratin. The ability to do this allows any of the active compounds (Formula I, Formula II) to be selected and modified to improve their ADME, PK and other properties, while still preserving the activity of the agent as it is eventually released as the free drug. The prodrug can be converted to the free drug while in transit to its target, for instance, after entering cells containing the target, etc. It could also be used to target cells after which the added acyl group falls off and the free drug acts upon the target cells.

As examples, the cleavable linkage may include a group that is hydrolyzable, enzymatically or otherwise cleavable in vivo, such as disulfide (which may be cleaved by the tripeptide glutathione), ester, thioester, amide, acid anhydride, or the like. The cleavable linkage may also be formed by oligonucleotides with a restriction site, peptides with a protease cleavage site, and the like. A cell uptake-facilitating moiety that can be used is a cationic peptide, such as nona-arginine (see Biochemistry. 01/04/200404/2004; 43(9):2438-44), or other oligoarginine peptides, as well as TAT peptides such as KKRRQRRR or subsequences thereof.

Synthesis

The present disclosure describes synthetic methods for preparing the above-mentioned C20 prodrugs of the PKC modulators of the present disclosure. Methods for synthesizing C13 analogs is disclosed in U.S. Pat. No. 8,816,122, which is specifically incorporated herein by reference, as setting forth synthetic methods yielding analogs of the PKC modulators of the present disclosure. Synthesis procedures for embodiments of the prodrugs of the present disclosure are also presented in the Examples below.

Prodrugs of prostratin, ingenol, and the novel compounds disclosed herein are advantageous in that many of the present compounds may be, and prostratin is known to be, inflammatory at the site of administration (e.g., injection). Since the present compounds activate PKC, they may be expected to cause inflammation at the site of administration, i.e., injection. By preparing a prodrug that does not have PKC activation activity, the compound may be diffused through the body while it is being activated, lessening the acute inflammatory response and enabling a more rapid administration, such as a bolus injection rather than a prolonged drip.

Figure 11A:
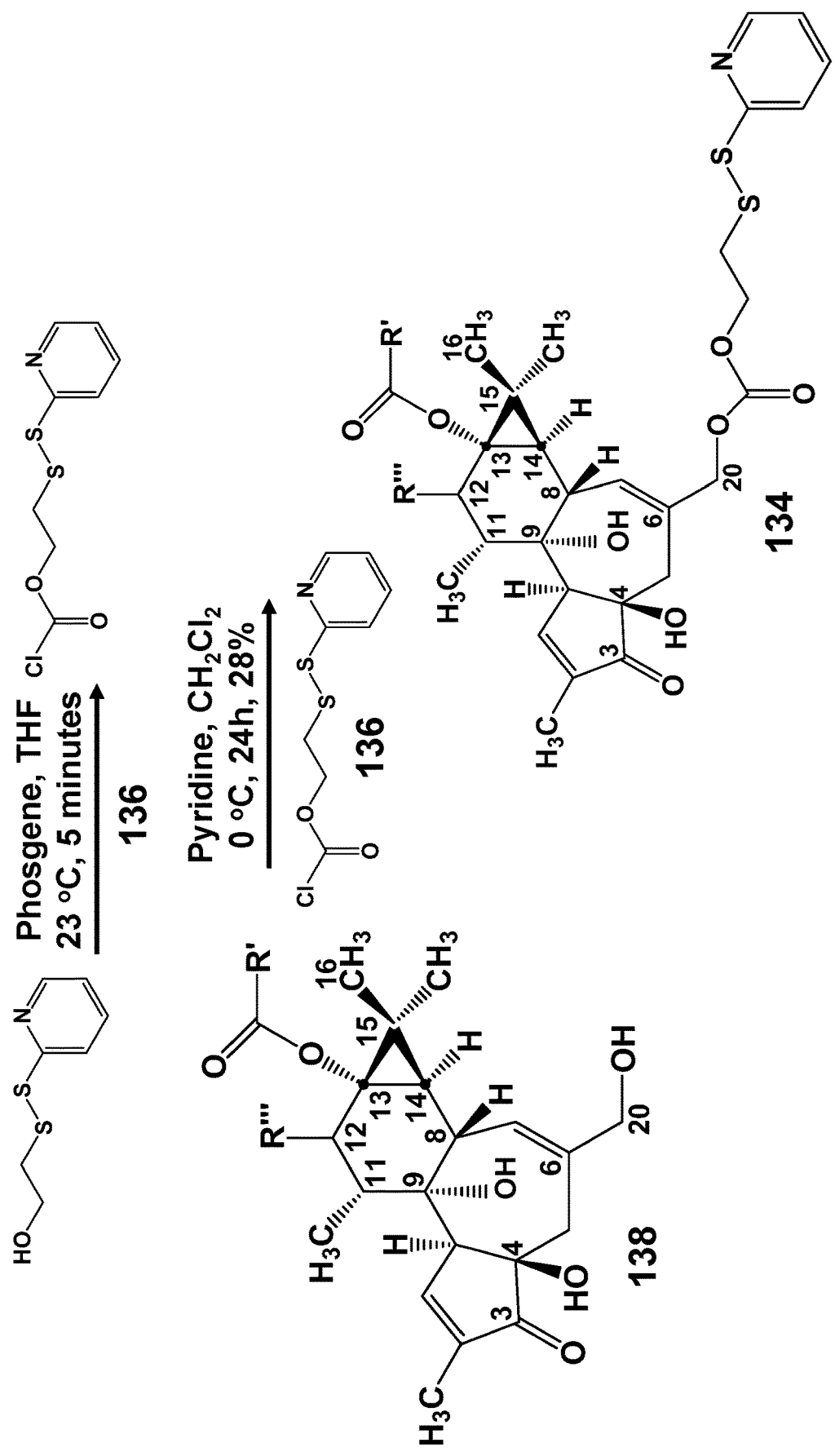
FIGS. 11A and 11B illustrate methods for making an exemplary phorbol ester prodrugs including an ester, an ester and disulfide linkages, and further including an oligopeptide (eight arginine residues).
Figure 11B:
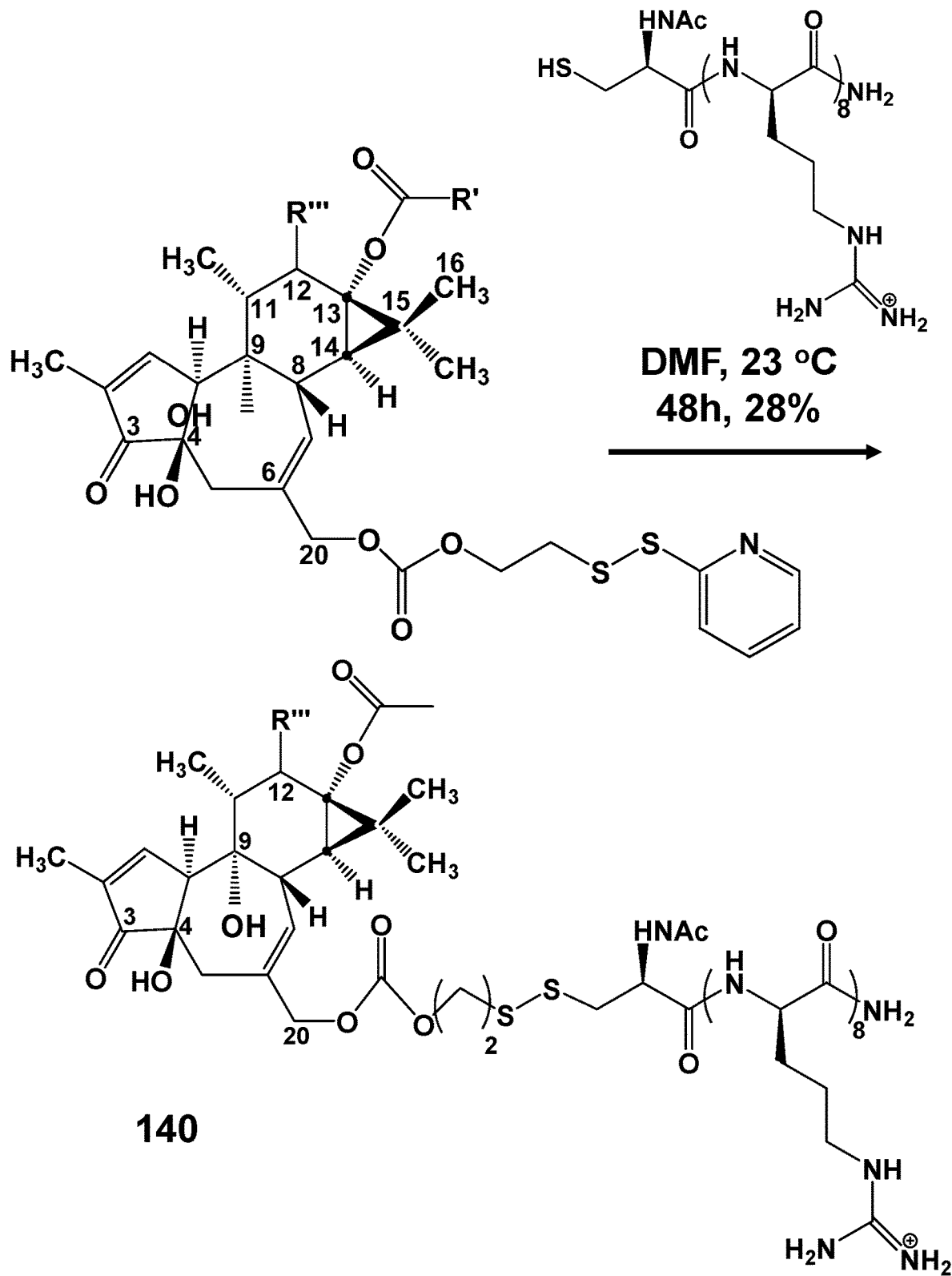

An alteration in the C20 of prostratin or ingenol and analogs thereof, or of the equivalent position in other PKC modulators as herein described, is employed to provide a group in place of the C20 hydroxyl or as a substituent of the C20-oxygenation that is required for activity, yet is processed in vivo to produce the C20 hydroxyl. As shown in FIG. 11A, a 2-thiopyridine connected through a disulfide linkage to an alkyl alcohol can be reacted with phosgene or an equivalent thereof, for example, but not limited to, triphosgene to produce the corresponding alkylcarbono chloridate. This is linked to the hydroxyl group at C20 of prostratin and analogs thereof of the equivalent position other PKC modulators, in step 2. Then, in step 3, shown in FIG. 11B, the product of step 2 can be reacted with AcNH-D-Cys-(DArg)$_8$CONH$_2$ in DMF, for 48 hr. This compound has been shown to convert to the parent prostratin or prostratin analog within two minutes with full release after 15 minutes. The disulfide group facilitates cleavage of the carbonate structure to yield the C20 alcohol. The method may be generally applicable to carbonates and similar groups where the carbonate comprises instead the general structure —O—C(=O)—O—R, where the O is attached to the C20 carbon and the R may be a variety of alkyl, aryl and heteroaryl groups.

Pharmaceutical Compositions: Administration of the active compounds and salts described herein can be via any of the accepted modes of administration for therapeutic agents. These methods include oral, parenteral, transdermal, subcutaneous and other systemic modes. In some instances it may be necessary to administer the composition parenterally.

Depending on the intended mode, the compositions may be in the form of solid, semisolid or liquid dosage forms, such as, for example, tablets, suppositories, pills, capsules, powders, liquids, suspensions, skin patch, or the like, preferably in unit dosage forms suitable for single administration of precise dosages. The compositions can include a conventional pharmaceutical excipient and an active compound of the present disclosure or the pharmaceutically acceptable salts thereof (e.g., ingenol, prostratin, bryostatin, and their analogs) and, in addition, may include other medicinal agents, pharmaceutical agents, carriers, adjuvants, diluents, etc.

Embodiments of the compounds of the present disclosure are typically administered to a patient in the form of a pharmaceutical composition or formulation. Such pharmaceutical compositions can be administered to the patient by any acceptable route of administration including, but not limited to, oral, rectal, vaginal, nasal, inhaled, topical (including transdermal) and parenteral modes of administration.

Accordingly, an embodiment of the present disclosure is directed to a pharmaceutical composition comprising a pharmaceutically-acceptable carrier or excipient and a therapeutically effective amount of a compound of the present disclosure or a pharmaceutically acceptable salt thereof.

Optionally, such pharmaceutical compositions may contain other therapeutic and/or formulating agents if desired. When discussing compositions, the "compound of the present disclosure" may also be referred to herein as the "active agent" or "agent". As used herein, the term "compound of the present disclosure" is intended to include a novel compound described in formulae provided herein and in the claims (e.g., ingenol, prostratin, bryostatin, and their analogs).

The pharmaceutical compositions of the present disclosure typically contain a therapeutically effective amount of a compound of the present disclosure or a pharmaceutically-acceptable salt thereof. Typically, such pharmaceutical compositions can contain about 0.1 to about 95% by weight of the active agent; preferably, about 5 to about 70% by weight; and more preferably about 10 to about 60% by weight of the active agent.

A conventional carrier or excipient can be used in the pharmaceutical compositions of the present disclosure. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this present disclosure are commercially-available. By way of further illustration, conventional formulation techniques are described in Remington: The Science and Practice of Pharmacy, 20$^{th}$ Edition, Lippincott Williams & White, Baltimore, Md. (2000); and H. C. Ansel et al., Pharmaceutical Dosage Forms and Drug Delivery Systems, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other nontoxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the present disclosure are preferably packaged in a unit dosage form. The term "unit dosage form" refers to a physically discrete unit suitable for dosing a patient, e.g., each unit containing a predetermined quantity of active agent (e.g., prostratin, bryostatin, and their analogs) calculated to produce the desired therapeutic effect either alone or in combination with one or more additional units. For example, such unit dosage forms can be capsules, tablets, pills, and the like, or unit packages suitable for parenteral administration.

In an embodiment, the pharmaceutical compositions of the present disclosure are suitable for oral administration. Suitable pharmaceutical compositions for oral administration can be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present disclosure as an active ingredient.

When intended for oral administration in a solid dosage form (i.e., as capsules, tablets, pills and the like), the pharmaceutical compositions of the present disclosure can typically include the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the present disclosure. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid-methacrylic acid ester copolymers, cellulose acetate trimellitate, carboxymethyl ethyl cellulose, hydroxypropyl methyl cellulose acetate succinate, and the like.

Pharmaceutical compositions of the present disclosure may also be formulated to provide slow or controlled release of the active agent using, by way of example, hydroxypropyl methyl cellulose in varying proportions; or other polymer matrices, liposomes and/or microspheres. In addition, the pharmaceutical compositions of the present disclosure may optionally contain opacifying agents and can be formulated so that they release the active ingredient only, or preferentially, in a certain portion of the gastrointestinal tract, optionally, in a delayed manner. Examples of embedding compositions which can be used include polymeric substances and waxes. The active agent can also be in microencapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of the present disclosure can also be administered parenterally (e.g., by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations can be rendered sterile by use of a sterile injectable medium, a sterilizing agent, filtration, irradiation, or heat.

Alternatively, the pharmaceutical compositions of the present disclosure are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the present disclosure will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition can be in the form of a capsule or cartridge (made, for example, from gelatin) comprising a compound of the present disclosure and a powder suitable for use in a powder inhaler. Suitable powder bases include, by way of example, lactose or starch.

The compounds of the present disclosure can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, can be used in such transdermal compositions if desired.

If desired, the compounds of this present disclosure can be administered in combination with one or more other therapeutic agents. In this embodiment, a compound of this present disclosure is either physically mixed with the other therapeutic agent to form a composition containing both agents; or each agent is present in separate and distinct compositions which are administered to the patient simultaneously or sequentially.

For example, a compound of the present disclosure can be combined with a second therapeutic agent using conventional procedures and equipment to form a composition comprising a compound of the present disclosure (e.g., prostratin, bryostatin, and their analogs) and a second therapeutic agent. Additionally, the therapeutic agents can be combined with a pharmaceutically acceptable carrier to form a pharmaceutical composition comprising a compound of the present disclosure, a second therapeutic agent and a pharmaceutically acceptable carrier. In this embodiment, the components of the composition are typically mixed or blended to create a physical mixture. The physical mixture is then administered in a therapeutically effective amount using any of the routes described herein. Alternatively, the therapeutic agents may remain separate and distinct before administration to the patient. In this embodiment, the agents are not physically mixed together before administration but are administered simultaneously or at separate times as separate compositions. Such compositions can be packaged separately or can be packaged together as a kit. The two therapeutic agents in the kit can be administered by the same route of administration or by different routes of administration. Any therapeutic agent compatible with the compounds of the present disclosure can be used as the second therapeutic agent.

In an embodiment, multiple doses of the agent (e.g., ingenol, prostratin, bryostatin, and their analogs and/or prodrugs thereof) are contacted (e.g., administered). The frequency of administration of the agent can vary depending on any of a variety of factors, e.g., severity of the symptoms, and the like. For example, in an embodiment, the agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the agent is administered continuously.

The duration of contact (e.g., administration) of the agent, e.g., the period of time over which the agent is administered, can vary, depending on any of a variety of factors, e.g., patient response, etc. For example, the agent can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art.

In an embodiment of the present disclosure, an effective dosage may be in the range of 0.001-100 mg/kg/day, preferably 0.005-5 mg/kg/day. For an average 70 kg human, this would amount to 0.007-7000 mg per day, or preferably 0.05-350 mg/day. Alternatively, the administration of compounds as described by L.C. Fritz et al. in U.S. Pat. No. 6,200,969 is followed. One of skill in the art with this disclosure can create an effective pharmaceutical formulation.

Methods of Use

Embodiments of the present compounds (e.g., ingenol analogs, prostratin analogs, and prodrugs thereof) have been shown to have activity in the following applications: (1) binding to protein kinase C; (2) J-Lat cell line and human PBMC latent virus induction; and/or (3) in vivo activation of CD4+ T-cells in C57/bl6 mice. In particular, embodiments of the compounds, when administered to an animal or human and cleaved to release the masking group, can exhibit activity against human immunodeficiency virus (HIV), stimulate transcription of proviral HIV DNA; and/or bind to protein kinase C. Additional details are provided in the Examples.

In general, the compounds of the present disclosure and pharmaceutical compositions thereof can be useful in treating disease caused by HIV, in particular AIDS. The treatment methods typically comprise administering to a subject (e.g., human) infected with such virus a therapeutically effective amount of a compound of the present disclosure in one or more doses, alone or in combination with other agents (e.g., drugs or biologicals). For example, one or more compounds of the present disclosure is provided or administered to a subject infected with HIV in an amount effective to result in the treatment of HIV or AIDS. In an embodiment, one or more compounds of the present disclosure can be used in combination with other HIV/AIDS drugs or biologicals.

The present disclosure also provides methods of prophylactically treating an infection by a HIV virus comprising administering an effective amount of a compound of the present disclosure in one or more doses, alone or in combination with other agents (e.g., drugs or biologicals) to a subject in need thereof.

Accordingly, one aspect of the present disclosure encompasses embodiments of a compound having the formula I:

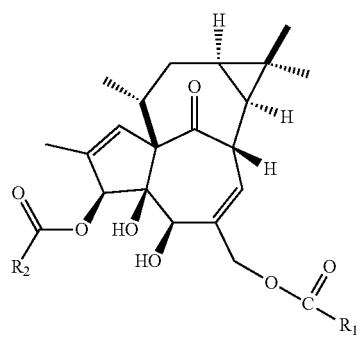

wherein: $R_1$ can be selected from the group consisting of: an alkyl, an aryl, an alkoxy, —NH-alkyl; and $R_2$ can be selected from the group consisting of: a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, $R_1$ is a nonyl ($C_9H_{19}$) group and $R_2$ is para-bromo-ortho-methylphenyl group.

Another aspect of the disclosure encompasses embodiments of a therapeutic composition comprising a protein kinase C (PKC) agonist prodrug in an amount therapeutically effective when delivered to an animal or human subject, wherein the PKC agonist prodrug has the formula I or II:

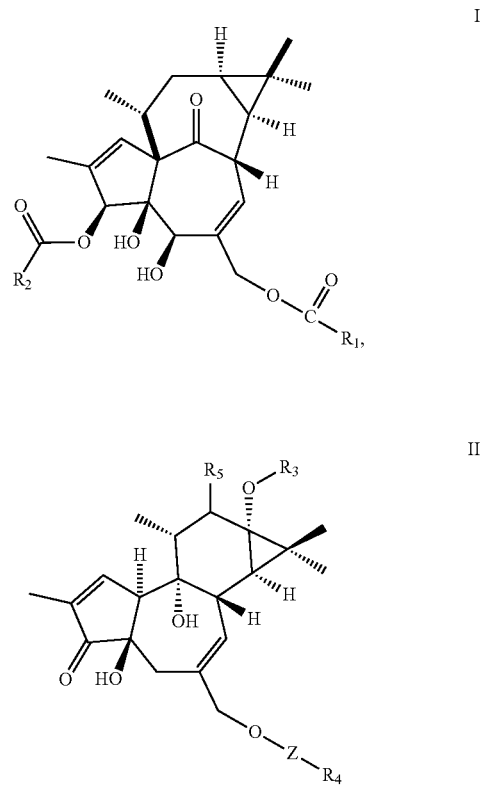

wherein: Z can be a cleavable linkage; $R_1$ and $R_2$ can each be independently selected from the group consisting of: a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl; $R_3$ and $R_5$ are each independently selected from the group consisting of: H, a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl; and $R_4$ can be selected from the group consisting of: a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, the PKC agonist prodrug can have the formula I:

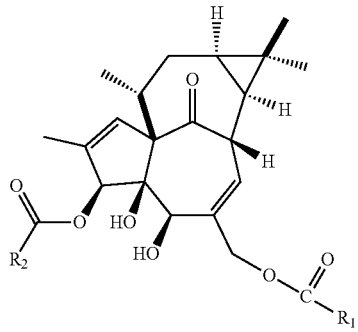

wherein $R_1$ can be a nonyl ($C_9H_{19}$) group and $R_2$ can be selected from the group consisting of: a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, the PKC agonist prodrug can have the formula I:

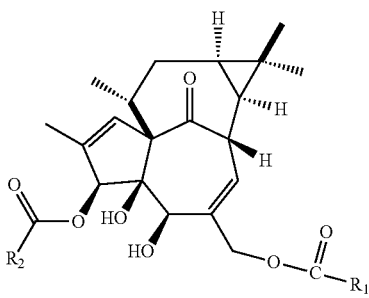

wherein $R_1$ can be a nonyl ($C_9H_{19}$) group and $R_2$ can be para-bromo-ortho-methylphenyl group.

In some embodiments of this aspect of the disclosure, the PKC agonist prodrug can have formula II and $R_5$ can be H.

In some embodiments of this aspect of the disclosure, $R_3$ is —CO-tricyclo[3.3.1.1$^{3.7}$]decane (—CO-adamantane), and the PKC agonist prodrug has formula:

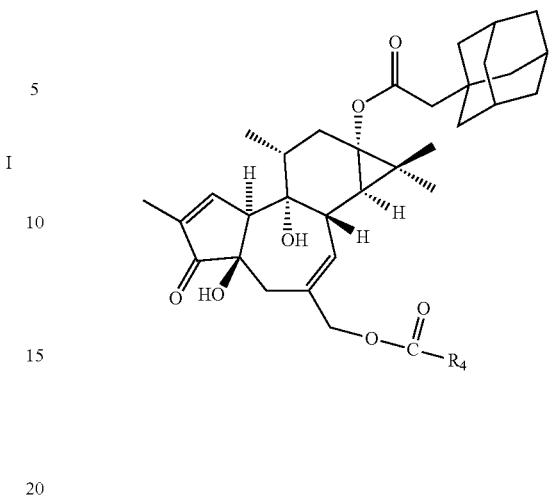

wherein: $R_4$ can be selected from the group consisting of: a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, the PKC agonist prodrug can have the formula II and $R_4$ can be methyl, pentyl, nonyl, phenyl, ethoxy, or octylamine.

In some embodiments of this aspect of the disclosure, the therapeutic composition can further comprise a pharmaceutically acceptable carrier.

In some embodiments of this aspect of the disclosure, the composition can be formulated for delivery of an effective dose of the protein kinase C (PKC) agonist prodrug to a patient in need thereof intravenously, intraparentally, subcutaneously, intramuscularly, orally, or by inhalation.

Still another aspect of the disclosure encompasses embodiments of a method of modulating the activity of a protein kinase C (PKC) in an animal or human cell comprising contacting an animal or human cell with a pharmaceutically acceptable composition comprising a PKC agonist prodrug having the formula I or II:

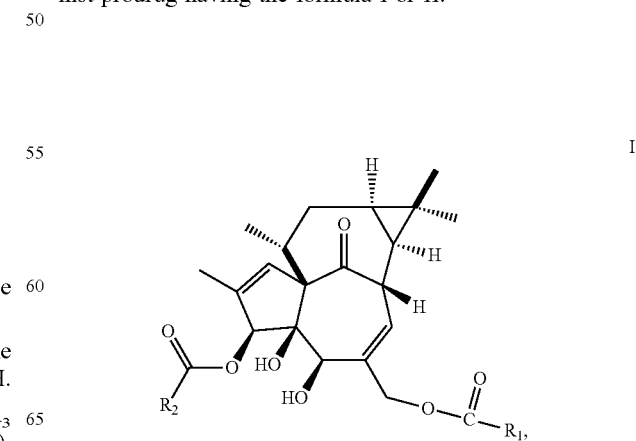

-continued

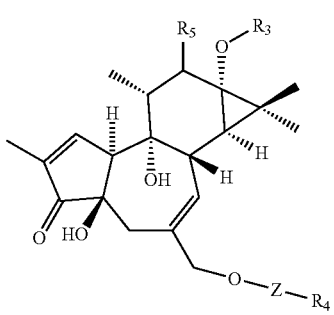

wherein: Z can be a cleavable linkage; $R_1$ can be can be selected from the group consisting of: a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl; $R_2$ can be selected from the group consisting of: a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl; $R_3$ and $R_5$ are each independently selected from the group consisting of: H, a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl; and $R_4$ can be selected from the group consisting of: a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, the PKC agonist prodrug can have the formula I:

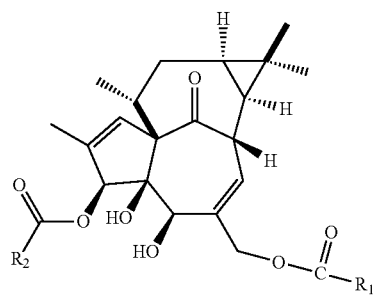

wherein $R_1$ can be a nonyl ($C_9H_{19}$) group and $R_2$ can be selected from the group consisting of: a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, the PKC agonist prodrug has the formula I:

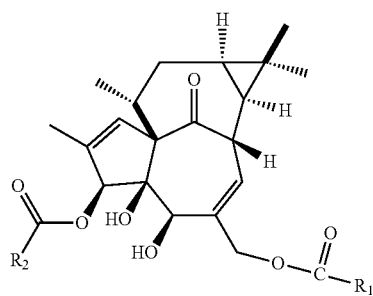

wherein $R_1$ can be a nonyl ($C_9H_{19}$) group and $R_2$ is para-bromo-ortho-methylphenyl group. In some embodiments of this aspect of the disclosure, the PKC agonist prodrug can have formula II and $R_5$ can be H.

In some embodiments of this aspect of the disclosure, $R_3$ is —CO-tricyclo[3.3.1.1$^{3.7}$]decane (—CO-adamantane), and the PKC agonist prodrug has formula:

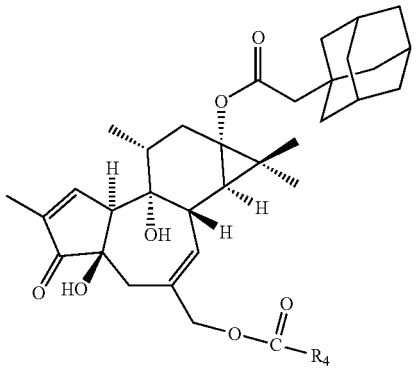

wherein: $R_4$ can be selected from the group consisting of: a substituted or unsubstituted —CO-bridged hydrocarbon, a substituted or unsubstituted alkyl, a substituted or unsubstituted aryl, a substituted or unsubstituted cycloalkyl, a substituted or unsubstituted cycloalkenyl, a substituted or unsubstituted aryl, a substituted or unsubstituted biaryl, a substituted or unsubstituted fused aryl, a substituted or unsubstituted alkenyl, and a substituted or unsubstituted alkynyl.

In some embodiments of this aspect of the disclosure, the PKC agonist prodrug can have the formula II and $R_4$ can be methyl, pentyl, nonyl, phenyl, ethoxy, or octylamine.

In some embodiments of this aspect of the disclosure, the pharmaceutically acceptable composition can be administered to an animal or human subject.

In some embodiments of this aspect of the disclosure, the pharmaceutically acceptable composition can be formulated for delivery to a patient in need thereof intravenously, intraparentally, subcutaneously, intramuscularly, orally, or by inhalation.

As mentioned above, compounds of the present disclosure and pharmaceutical compositions can be used in combination of one or more other therapeutic agents for treating viral infection and other diseases. For example, compounds of the present disclosure and pharmaceutical compositions provided herein can be employed in combination with other anti-viral agents to treat viral infection.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

General Methods: Unless otherwise specified, all reactions were carried out in an oven-dried (>110° C.) round-bottom flask equipped with a Teflon®-coated magnetic stir bar and a rubber septum under a positive pressure of argon. Sensitive solvents and reagents were transferred by syringe or stainless steel cannula. Reactions were run at room temperature unless otherwise stated. The pH was controlled by the reaction conditions and not checked or adjusted. Unless otherwise specified, reaction temperatures refer to the external temperatures of the bath in which the reaction vessel was partially immersed. The term "0° C." refers to an ice water bath.

The terms "removal of the solvent in vacuo" and "concentration" refer to evaporation of solvent using a rotary evaporator equipped with a vacuum pump. Residual solvents were removed from nonvolatile samples using a vacuum line held at 0.1-1.0 mm Hg.

Reagents and Solvents: The starting material compounds, solvents, reagents, etc. described herein are available from commercial sources or are easily prepared from literature references by one of skill in the art. See Chem Sources USA, published annually by Directories Publications, Inc. of Boca Raton, Fla. Also see The Aldrich Chemical Company Catalogue, Milwaukee, Wis. The starting materials were used as obtained unless otherwise noted. Dichloromethane and toluene were passed through an alumina drying-column. Pyridine and diisopropylmethane were distilled from calcium hydride under nitrogen. Denatured chloroform was passed through a pad of basic alumina and stored over anhydrous potassium.

Chromatography: Analytical thin-layer chromatography (TLC) was performed by using glass or aluminum-backed silica plates coated with a 0.25 mm thickness of silica gel 60 F254 (Merck), visualized with an ultraviolet light, followed by exposure to p-anisaldehyde solution, potassium permanganate solution, or ceric ammonium molybdate solution and heating.

The term "flash column chromatography" refers to column chromatography using Merck silica gel 60 (230-400 mesh) as described by Still et al., (1978) *J. Org. Chem.*, 43: 2923-2925. The eluent composition is indicated following the description of purification (percentage of the more polar solvent in the less polar solvent). The size of the column, the amount of silica gel loaded and the volume of eluent required for packing and elution were chosen based on the method described by Still.

Example 2

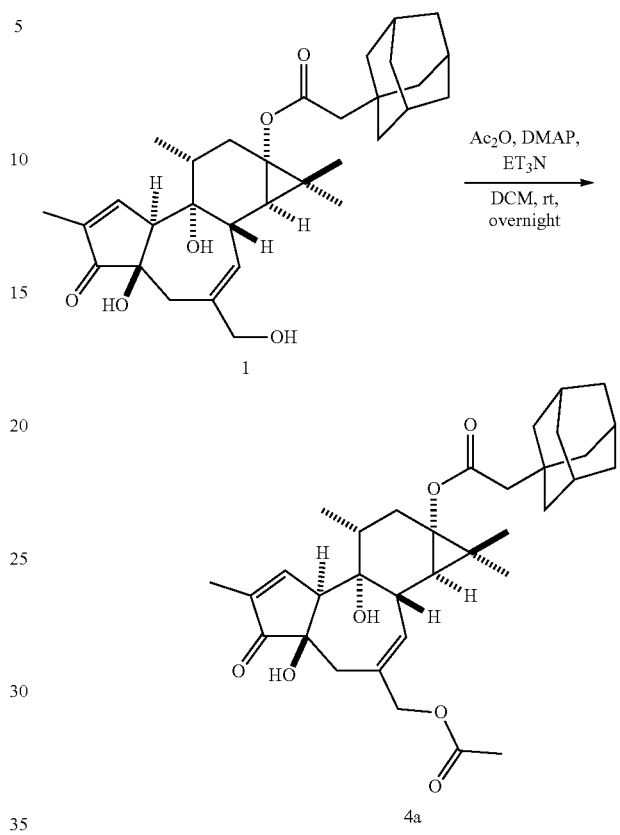

Synthesis of 4a: To a solution of 1 (5 mg, 0.01 mmol) in dichloromethane (0.5 mL) was added DMAP (1.3 mg, 0.01 mmol), triethylamine (3 µL, 0.02 mmol), and acetic anhydride (2 µL, 0.02 mmol). The reaction was stirred under inert atmosphere at room temperature overnight. The reaction mixture was diluted with dichloromethane (5 mL), and sequentially washed with saturated sodium bicarbonate, water, and saturated sodium chloride (5 mL each). The organics were separated and dried over $Na_2SO_4$ and concentrated in vacuo to a clear oil. Flash chromatography (35% EtOAc in pentane) yielded pure 4a as a white powder (7 mg, quant. yield).

Example 3

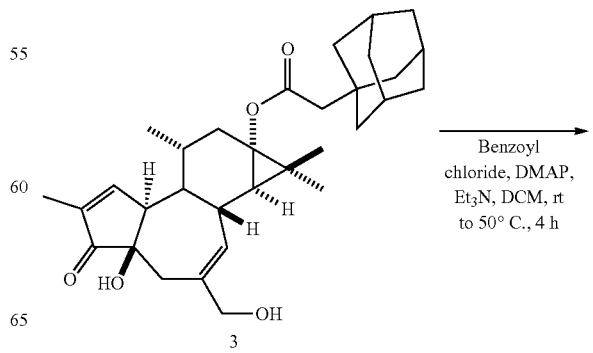

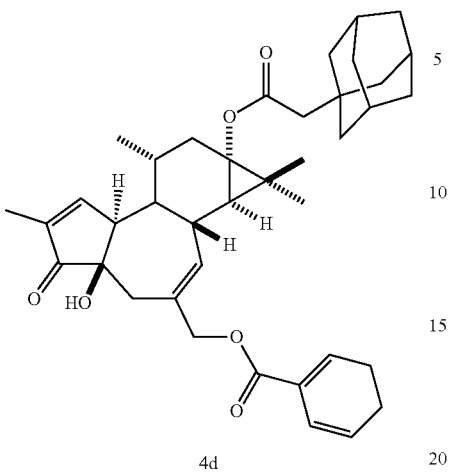

4d

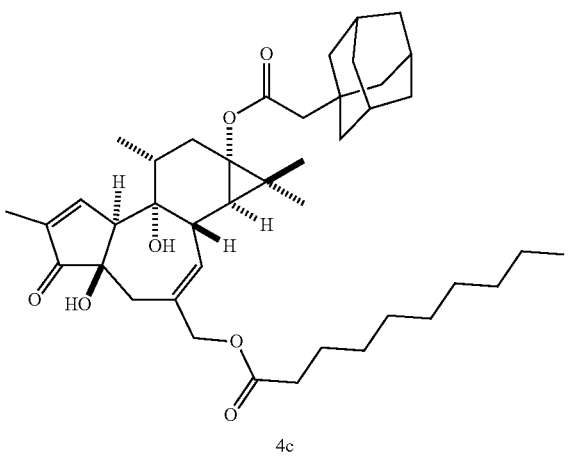

4c

Synthesis of 4b: Starting material 1 (0.019 mmol, 10 mg) was added to an oven dried vial equipped with a stir bar under nitrogen and dissolved in DCM (1.5 ml). To this was added triethylamine (0.038 mmol, 5.3 µl) followed by hexanoyl chloride (0.038 mmol, 5.4 µl). The reaction stirred for 2 hours at room temperature before being quenched by water and extracted three times with ethyl acetate. This was then washed with sodium bicarbonate and once with saturated sodium chloride. The organic layer was dried over anhydrous sodium sulfate, filtered, and the solvent was removed in vacuo. The crude product was purified by a silica gel chromatography (30% EtOAc/Pentane) to afford the product as a clear film (5.7 mg, 0.091 mmol, 48%, one spot by TLC).

Synthesis of 4c: To a solution of 1 (10 mg, 0.017 mmol) in dichloromethane (1 mL) was added DMAP (2.1 mg, 0.017 mmol), triethylamine (5 µL, 0.034 mmol), and decanoic anhydride (11 mg, 0.034 mmol). The reaction was stirred under inert atmosphere at room temperature overnight, whereupon the reaction solution turned a slight orange color. The reaction mixture was diluted with dichloromethane (5 mL), and sequentially washed with saturated sodium bicarbonate, water, and saturated sodium chloride (5 mL each). The organics were separated and dried over sodium sulfate and concentrated in vacuo to a faintly orange-colored paste. Flash chromatography (10% EtOAc in pentane) yielded pure 4c as a colorless oil (7 mg, 61% yield).

Example 4

Example 5

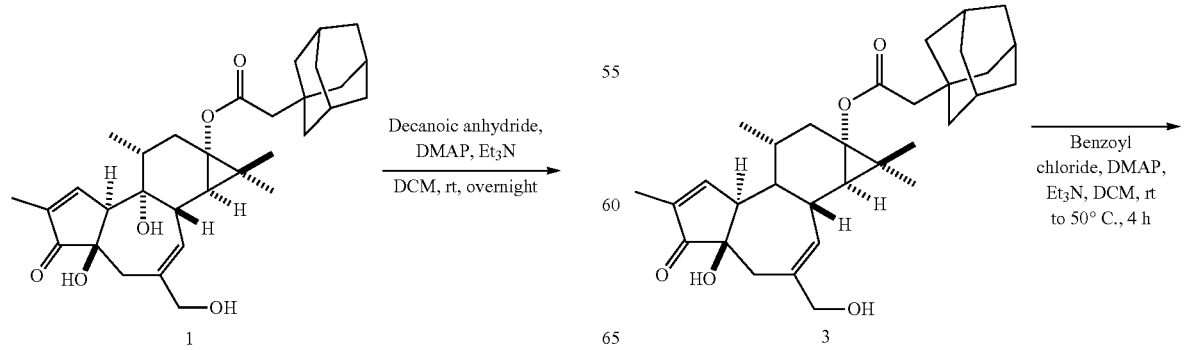

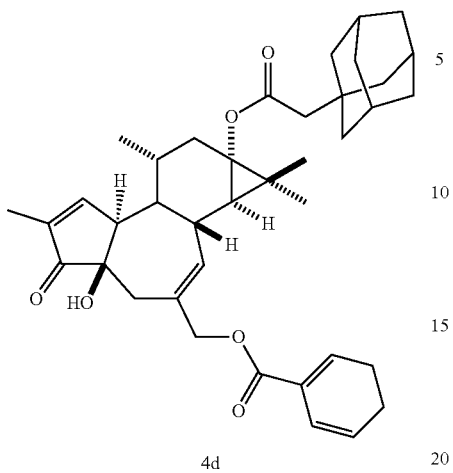

4d

Synthesis of 4d: Starting material 1 (0.019 mmol, 10 mg) was added to an oven dried vial equipped with a stir bar under nitrogen and dissolved in DCM (1.5 ml). To this was added triethylamine (0.038 mmol, 5.3 µl) followed by benzoyl chloride (0.038 mmol, 4.5 µl). The reaction stirred overnight at room temperature and quenched by water and extracted three times with ethyl acetate. This was then washed once with sodium bicarbonate and once with saturated sodium chloride. The organic layer was dried over anhydrous sodium sulfate, filtered, and the solvent was removed in vacuo. The crude product was purified by a silica gel chromatography (50% EtOAc/Pentane) to afford 4d as a clear film (6.7mg, 56% yield).

Example 6

4e

Synthesis of 4e: To a solution of 1 (10 mg, 0.017 mmol) in dichloromethane (0.3 mL) was added triethylamine (5 µL, 0.034 mmol), and ethyl chloroformate (3.25 µL, 0.034 mmol). The reaction was stirred for 4 h at room temperature, then DMAP (4 mg, 0.034 mmol) was added in one portion and the reaction was stirred for another 4 h, whereupon all starting material was consumed. The reaction mixture was diluted with dichloromethane (5 mL), and sequentially washed with saturated sodium bicarbonate, water, and saturated sodium chloride (5 mL each). The organics were separated and dried over magnesium sulfate and concentrated in vacuo to a clear oil. Flash chromatography (20% ethyl acetate in pentane) yielded pure 4e as a colorless oil (3 mg, 30% yield).

Example 7

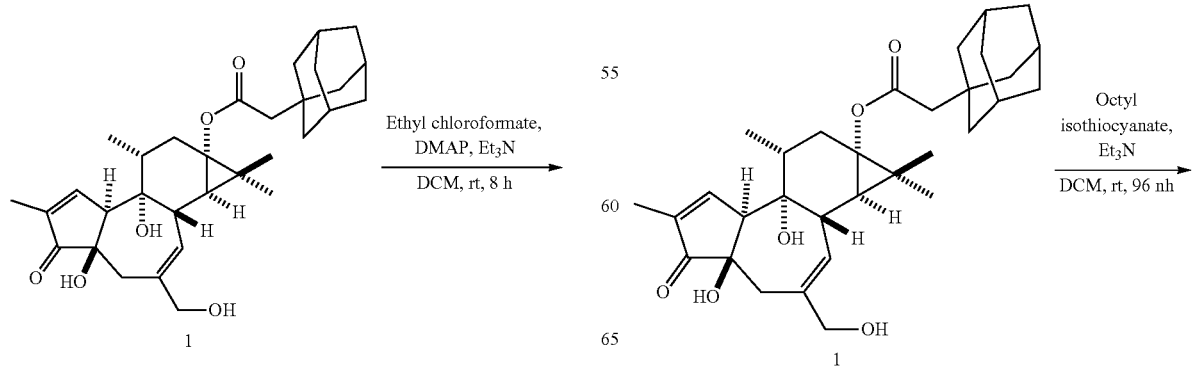

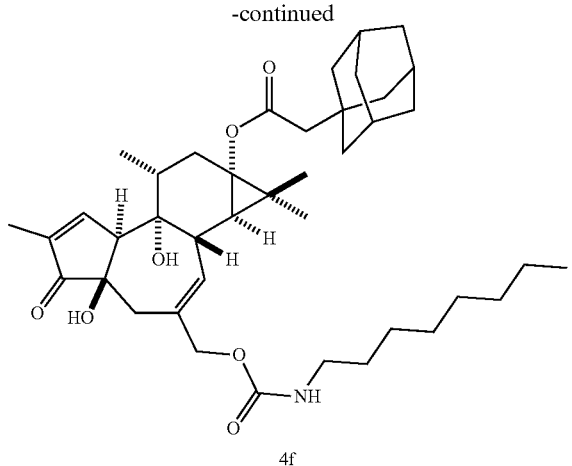

4f

Synthesis of 4f: To a solution of 1 (11 mg, 0.021 mmol) in dichloromethane (2 mL) was added triethylamine (18.6 µL, 0.133 mmol), and octyl isocyanate (14.4 µL, 0.0136 mmol). The reaction was stirred for 96 h at room temperature until all starting material consumed by TLC. The reaction mixture was concentrated in vacuo and purified by flash chromatography. Flash chromatography (20%-50% ethyl acetate in pentane) yielded 4f as a white solid (8.6 mg, 60.3% yield).

Example 8

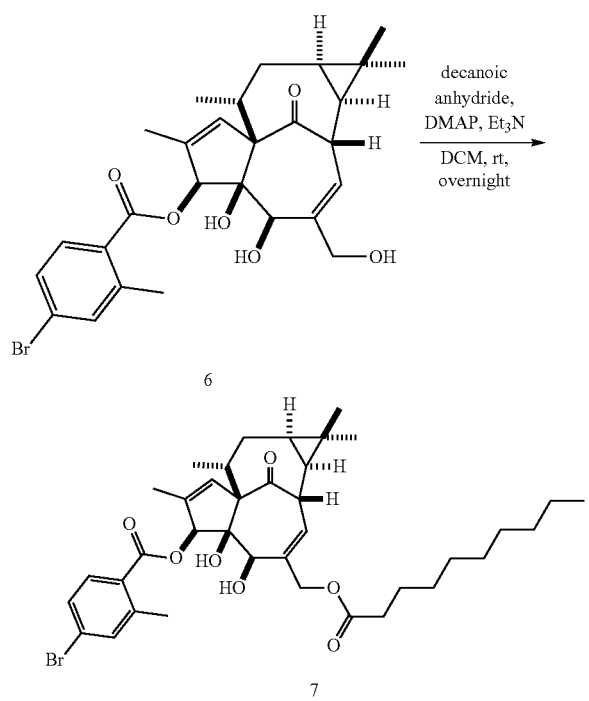

Synthesis of 7: To a solution of 6 (1.5 mg, 2.8 µmol) in dichloromethane (150 µL) was added DMAP (0.5 mg, 5.7 µmol), decanoic anhydride (2.0 mg, 6.2 µmol), and triethylamine (0.8 µL, 5.7 µmol). The reaction was stirred under inert atmosphere at room temperature overnight. The reaction mixture was diluted with dichloromethane (750 µL), and sequentially washed with saturated aqueous sodium bicarbonate, water, and saturated sodium chloride (750 µL each). The combined organic layers were dried over sodium sulfate, filtered, and concentrated in vacuo to a colorless oil. Flash chromatography (0%-30% ethyl acetate in pentane) yielded pure 4 as a colorless oil (1.2 mg, 63% yield).

Example 9

Hydrolytic Stability Assay: A solution of 400 µM of parent compound or prodrug derivative with 2,4,6-trimethylphenol (800 µM, 107 µg) in HEPES buffered saline, pH 7.4, with 10% DMSO (total volume 1000 µL) was incubated at 37° C. At appropriate time points, 100 µL was removed, flash frozen, and lyophilized. The lyophilized material was then diluted with 100 µL acetonitrile, filtered, and analyzed by analytical HPLC. The degree of degradation was calculated relative to the area under the curve of the compound of interest compared to the internal standard, 2,4,6-trimethylphenol, as shown in Table 1.

Porcine Liver Esterase Assay: A solution of 400 µM of parent compound or prodrug derivative with 2,4,6-trimethylphenol (800 µM, 160 µg) and 60 units of porcine liver esterase in HEPES buffered saline, pH 7.4, with 10% DMSO (total volume 1500 µL) was incubated at 37° C. At appropriate time points, 150 µL was removed, flash frozen, and centrifuged at 10,000 rpm. 140 µL of the supernatant was removed and lyophilized. The lyophilized material was then diluted with 100 µL acetonitrile, filtered, and analyzed by analytical HPLC. The degree of esterase cleavage was calculated relative to the area under the curve of the compound of interest compared to the internal standard, 2,4,6-trimethylphenol. The results of these studies are reported in Table 1 below.

TABLE 1

| | R | Yield | Hydrolytic stability ($t_{1/2}$) | Esterase stability ($t_{1/2}$)* |
|---|---|---|---|---|
| 3 | H | — | >7 d | 18 ± 3 h |
| 4a | ‒C(=O)‒ | quant. | >7 d | 27 ± 3 h |
| 4b | ‒C(=O)‒$C_5H_{11}$ | 48% | >74 d | 2.4 ± 0.5 h |
| 4c | ‒C(=O)‒$C_9H_{19}$ | 85% | >7 d | 19 ± 2 h |
| 4d | ‒C(=O)‒Ph | 56% | >7 d | 32 ± 9 h |
| 4e | ‒C(=O)‒O‒Et | 30% | >7 d | 4.8 ± 0.6 h |

TABLE 1-continued

| | R | Yield | Hydrolytic stability ($t_{1/2}$) | Esterase stability ($t_{1/2}$)* |
|---|---|---|---|---|
| 4f | 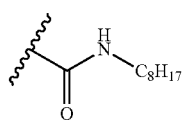 | 60% | >7d | 71 ± 13 h |
| 6 | H | — | 18 h | 1 h |
| 7 | 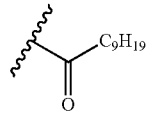 | 63% | 2 h | 2 h |

Example 10

Testing of Compounds for PKC Binding Affinity: A heterogeneous competitive radioligand assay against $^3$H-phorbol-12,13-dibutyrate ($^3$H-PDBu) was used to generate PKC binding constant ($K_i$) values. In a typical assay, a specific full-length PKC isoform was combined with Tris-HCl, KCl, CaCl$_2$, bovine serum albumin, water, and phosphatidyl serine. Serial dilutions of the respective analog were added to the PKC mixture; in addition, a solution of a compound with known PKC binding affinity and a solution containing no sample were added for reference.

After addition of [$^3$H]PDBu, these samples were incubated, filtered through filters previously wetted with polyethyleneimine and the filters were washed with Tris buffer. The filters were then placed into scintillation vials which were then filled with Bio-Safe scintillation fluid and were measured for radioactivity using a Beckman LS 6000SC scintillation counter. Counts per minute (cpm) were averaged for each triplicate dilution. The data was then plotted (cpm vs. log(concentration)) using Prism® by GraphPad Software and an IC$_{50}$ was determined using that program's built-in one-site competition least squares regression function. $K_i$ values were calculated by the equation: $K_i=IC_{50}/(1+[^3H\text{-PDBu}]/K_D \text{ of } ^3H\text{-PDBu})$. The $K_D$ of $^3$H-PDBu was measured via saturation binding under identical conditions and was found to be 1.55 to 4.4 nM, depending on batch-to-batch variability. The results of these studies are shown in Table 2.

TABLE 2

Binding affinities to PKCδ and PKCβI for prostratin and ingenol analogs
PKC binding affinity, $K_i$

| Analog | Novel PKCδ | Conventional PKCβI |
|---|---|---|
| 3 | 0.5 nM | 1.4 nM |
| 4a | 9.4 μM | — |
| 4b | >2.5 μM | >2.5 μM |
| 4c | 9.0 μM | |
| 4d | >2.5 μM | >0.5 μM |
| 4e | 380 nM | — |
| 4f | 2.9 μM | — |
| 6 | 1.1 nM | 0.85 nM |
| 7 | 11 μM | >19 mM |

Example 11

HIV Latency Induction Assay: J-Lat clone 10.6 cells were obtained from the AIDS Research and Reference Reagent Program, Division of AIDS, NIAID, NIH. These cells were cultured in RF10 media, consisting of RPMI Medium 1640 (Invitrogen) containing 10% fetal bovine serum (FBS, Omega Scientific) and 100 units/mL of penicillin+100 μg/mL of streptomycin (Pen/Strep, Invitrogen). The cells were incubated at 37° C. in 5% CO$_2$. During stimulation cells were seeded at a concentration of 50,000 cells/well in a V-bottomed 96-well plate containing the relevant concentration of compound in 100 μL of RPMI media. Cells were incubated for 48 h and then harvested by washing with fresh media and resuspending pellets in 2% paraformaldehyde. The percentage of GFP+ cells was quantified by flow cytometry using a LSRFortessa machine (BD Biosciences). The resultant list mode files were processed using FlowJo software (version 7.6).

An increase in the percent GFP$^+$ cells indicates induction of latent HIV expression, as J-Lat cells possess genomically encoded HIV-GFP fusion proteins. The results of this assay are shown in FIGS. 3A-3C and 4. Specifically, all of the aliphatic ester prodrugs (4a-4c, 7) exhibited an attenuated activation profile relative to the parent compounds (3, 6). Compounds 4d-4f, possessing less labile promoieties, showed no activity in this assay.

Example 12

Human PBMC CD69 Stimulation Assay: Peripheral blood mononuclear cells isolated using Ficoll-Paque Plus separation (GE Healthcare) from HIV sero-negative donors were obtained from the UCLA Virology Core. Cells were placed in V-bottomed 96-well plates at a density of 10$^5$ cells per well in a 200 μL volume of RF10 media containing the relevant concentration of compound. The cells were incubated at 37° C. in 5% CO$_2$. Cells were incubated for 48 h before harvesting for analysis using flow cytometry. Cells were first suspended in 50 μL of a 1:1 mix of 1× PBS and human AB serum (Sigma) and then stained with anti-human CD69-phycoerythrin (Beckman Coulter). Following antibody addition, the mixture was incubated at 4° C. for 15 min. The cells were then washed, resuspended in 1× PBS containing 2% paraformaldehyde, and stored at 4° C. Fixed cells were analyzed using an LSRFortessa (BD Biosciences). The resultant list mode files were processed using FlowJo software (version 7.6).

Upon activation of the NF-kB pathway, CD4$^+$ cells rapidly display early activation biomarker CD69. Thus observation of CD69 upregulation can be correlated with HIV latency reversal. The results of this assay are shown in FIGS. 5A-5C and 6. Trends similar to the results of the HIV latency induction assay were observed. Aliphatic ester prodrugs (4a-4c, 7) displayed attenuated CD69 upregulation compared to the parent compounds (3, 6), while prodrugs with more stable C20 protecting groups (4d-4f) displayed limited upregulation.

Example 13

In vivo C57/bl6 Mouse CD69 Stimulation Assay: C57/bl6 mice were obtained from the UCLA Department of Radiation Oncology. Prodrugs of the disclosure were administered intravenously via retro-orbital injection. At 24 h post-injection, mice were sacrificed and the spleens isolated. Spleens were disaggregated by forcing tissue through a steel mesh and then filtered through a 40 μm filter to produce a single-cell suspension. These cells were then stained for flow cytometry to analyze surface expression of relevant markers. Cells were first suspended in 50 μL of a 1:1 mix of 1× PBS and human AB serum (Sigma) and then stained with a combination of anti-mouse CD3-fluorescein isothiocyanate (eBioscience), CD69-phycoerythrin (eBioscience), and CD4-peridinin chlorophyll protein (eBioscience). Following antibody addition, the mixture was incubated at 4° C. for 15 min. The cells were then washed, resuspended in 1× PBS containing 2% paraformaldehyde, and stored at 4° C. Fixed cells were analyzed using an LSRFortessa (BD Biosciences). The resultant list mode files were processed using FlowJo software (version 7.6).

Figure 7:
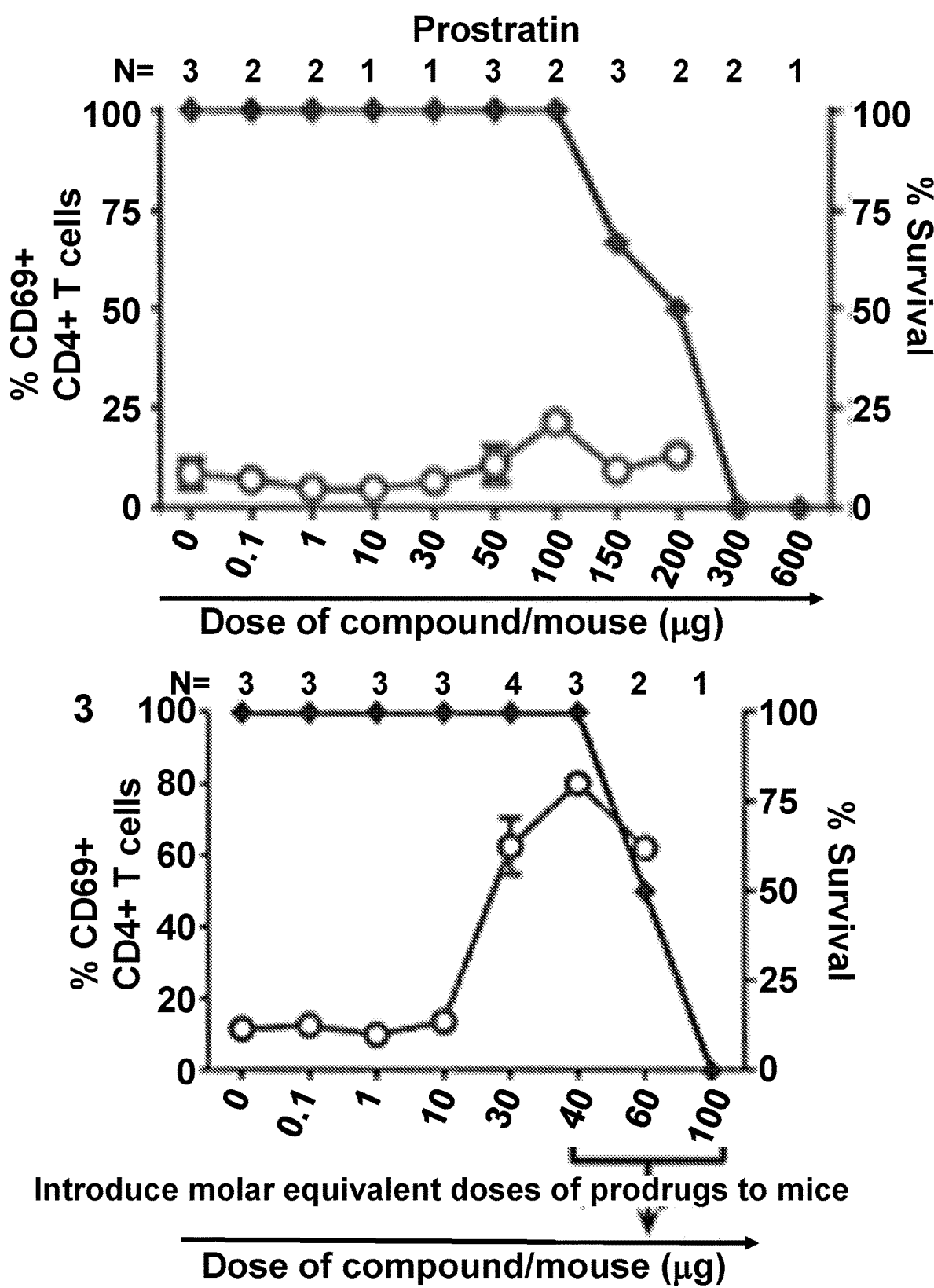
FIG. 7 shows a series of graphs that illustrate the in vivo activation of CD4+ T cells in C57/bl6 mice by different concentrations of the parent compound 3 and prodrug derivatives 4a and 4c, as well as the percent survival of mice administered with the compounds.

The results of this assay are shown in FIG. 7. The parent compound 1 displayed higher potency than prostratin but with a limited therapeutic window (one mouse casualty at 60 pg and no survival beyond that dose). However, all mice treated with either prodrug (4a or 4c) survived and showed strong stimulation of CD69 in splenocytes. CD69 expression was comparable for 4c and parent compound at the 60 µg dose, while 4a resulted in more moderate levels of activation. Percent survival of mice dosed with 4a or 4c indicated that the prodrugs have no bolus toxicity on mice even at the highest dosage.

What is claimed:

1. A compound having the formula I:

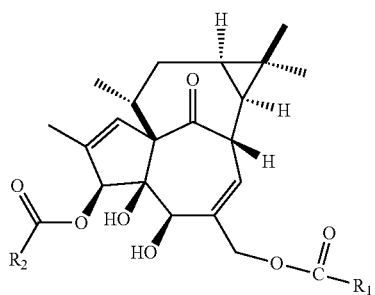

wherein, $R_1$ is a nonyl ($C_9H_{19}$) group and $R_2$ is para-bromo-ortho-methylphenyl group.

2. A pharmaceutically acceptable composition comprising a protein kinase C (PKC) agonist prodrug, wherein the PKC agonist prodrug has the formula I:

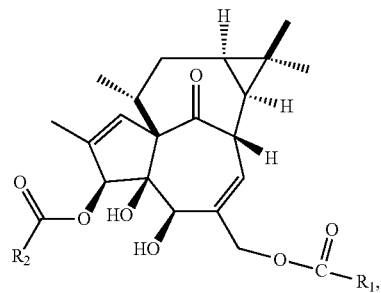

wherein $R_1$ is a nonyl ($C_9H_{19}$) group and $R_2$ is para-bromo-ortho-methylphenyl group, and a pharmaceutically acceptable carrier.

3. A method of modulating the activity of a protein kinase C (PKC) in an animal or human cell comprising contacting an animal or human cell with a pharmaceutically acceptable composition comprising a PKC agonist prodrug having the formula I:

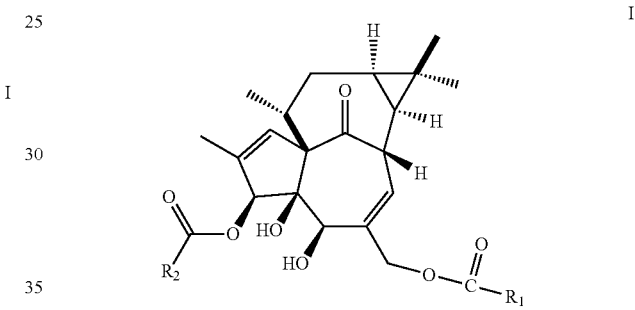

wherein $R_1$ is a nonyl ($C_9H_{19}$) group and $R_2$ is para-bromo-ortho-methylphenyl group.

4. The method of claim 3, wherein the pharmaceutically acceptable composition is administered to an animal or human subject.

5. The method of claim 3, wherein the pharmaceutically acceptable composition is formulated for delivery to a patient in need thereof intravenously, intraparentally, subcutaneously, intramuscularly, orally, or by inhalation.

* * * * *

UNITED STATES PATENT AND TRADEMARK OFFICE
CERTIFICATE OF CORRECTION

| | | |
|---|---|---|
| PATENT NO. | : 11,370,743 B2 | Page 1 of 1 |
| APPLICATION NO. | : 16/604665 | |
| DATED | : June 28, 2022 | |
| INVENTOR(S) | : Paul A. Wender et al. | |

It is certified that error appears in the above-identified patent and that said Letters Patent is hereby corrected as shown below:

In the Specification

Column 1, Line 5, add: "This invention was made with Government support under contracts CA031841 and CA031845 awarded by the National Institutes of Health. The Government has certain rights in the invention."

Signed and Sealed this
Thirtieth Day of September, 2025

John A. Squires
*Director of the United States Patent and Trademark Office*